United States Patent
Hirvelä et al.

(10) Patent No.: US 10,626,140 B2
(45) Date of Patent: Apr. 21, 2020

(54) PRODRUGS OF 17β-HSD1-INHIBITORS

(71) Applicant: FORENDO PHARMA LTD, Turku (FI)

(72) Inventors: Leena Hirvelä, Oulu (FI); Pasi Koskimies, Turku (FI); Risto Lammintausta, Turku (FI); Marjo Hakola, Kempele (FI); Maire Eloranta, Oulu (FI)

(73) Assignee: Forendo Pharma LTD (FI)

( * ) Notice: Subject to any disclaimer, the term of this patent is extended or adjusted under 35 U.S.C. 154(b) by 0 days.

(21) Appl. No.: 15/539,188

(22) PCT Filed: Dec. 22, 2015

(86) PCT No.: PCT/FI2015/050928
§ 371 (c)(1),
(2) Date: Jun. 23, 2017

(87) PCT Pub. No.: WO2016/102775
PCT Pub. Date: Jun. 30, 2016

(65) Prior Publication Data
US 2018/0265541 A1  Sep. 20, 2018

(30) Foreign Application Priority Data

Dec. 23, 2014  (FI) ................................... 20146149

(51) Int. Cl.

| C07J 43/00 | (2006.01) |
| C07J 51/00 | (2006.01) |
| A61P 3/04 | (2006.01) |
| A61P 5/24 | (2006.01) |
| A61P 13/02 | (2006.01) |
| A61P 17/02 | (2006.01) |
| A61P 19/02 | (2006.01) |
| A61P 27/12 | (2006.01) |
| A61P 35/00 | (2006.01) |

(52) U.S. Cl.
CPC .............. *C07J 43/003* (2013.01); *A61P 3/04* (2018.01); *A61P 5/24* (2018.01); *A61P 13/02* (2018.01); *A61P 17/02* (2018.01); *A61P 19/02* (2018.01); *A61P 27/12* (2018.01); *A61P 35/00* (2018.01); *C07J 51/00* (2013.01)

(58) Field of Classification Search
None
See application file for complete search history.

(56) References Cited

U.S. PATENT DOCUMENTS

| 2003/0170292 A1 | 9/2003 | Yong et al. |
| 2005/0192263 A1 | 9/2005 | Messinger et al. |
| 2006/0281710 A1 | 12/2006 | Messinger et al. |
| 2017/0081357 A1* | 3/2017 | Eloranta ................ C07J 43/003 |

FOREIGN PATENT DOCUMENTS

| CN | 1878786 A | 12/2006 |
| WO | WO 1999/046279 | 9/1999 |
| WO | WO 2000/007996 | 2/2000 |
| WO | WO 2001/042181 | 6/2001 |
| WO | WO 2003/022835 | 3/2003 |
| WO | WO 2003/033487 | 4/2003 |
| WO | WO 2004/046111 | 6/2004 |
| WO | WO 2004/060488 | 7/2004 |
| WO | WO 2004/085345 | 10/2004 |
| WO | WO 2004/085457 | 10/2004 |
| WO | WO 2004/110459 | 12/2004 |
| WO | WO 2005/032527 | 4/2005 |
| WO | WO 2005/047303 | 5/2005 |
| WO | WO 2005/084295 | 9/2005 |

(Continued)

OTHER PUBLICATIONS

Allan et al., "Modification of Estrone at the 6, 16, and 17 Positions: Novel Potent Inhibitors of 17β-Hydroxysteroid Dehydrogenase Type 1", *J. Med. Chem.*, vol. 49, No. 4., pp. 1325-1345, Jan. 2006.

(Continued)

*Primary Examiner* — Alicia L Otton
(74) *Attorney, Agent, or Firm* — Barnes & Thornburg LLP

(57) ABSTRACT

The present invention accordingly provides novel compounds of formula (I) wherein R1, R2, R3 and R4 are as defined in the claims. The invention further relates to their in treatment or prevention of steroid hormone dependent diseases or disorders, such as steroid hormone dependent diseases or disorders requiring the inhibition of the 17β-HSD1 enzyme and/or requiring the lowering of the endogenous estradiol concentration.

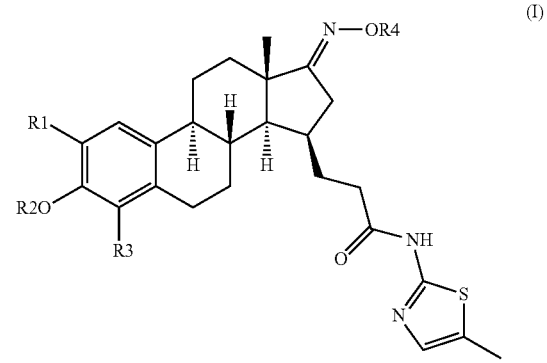

12 Claims, No Drawings

(56) References Cited

FOREIGN PATENT DOCUMENTS

| WO | WO 2006/003012 | 1/2006 |
| WO | WO 2006/003013 | 1/2006 |
| WO | WO 2006/027347 | 3/2006 |
| WO | WO 2006/125800 | 11/2006 |
| WO | WO 2008/034796 | 3/2008 |
| WO | WO 2008/065100 | 6/2008 |
| WO | WO 2014/207310 | 12/2014 |

OTHER PUBLICATIONS

Messinger et al., "Estrone C15 derivatives-A new class of 17β-hydroxysteroid dehydrogenase type 1 inhibitors", *Molecular and Cellular Endocrinology*, vol. 301, pp. 216-224, (2009).
Poirier, Donald, "Inhibitors of 17β-Hydroxysteroid Dehydrogenases", *Current Medicinal Chemistry*, vol. 10, No. 6; pp. 453-477; (2003).
Poirier, Donald, "17β-Hydroxysteroid dehydrogenase inhibitors: a patent review", *Expert Opin. Ther. Patents*, 20(9), pp. 1123-1145; (2010).
Puranen et al., "Site-directed mutagenesis of the putative active site of human 17β-hydroxysteroid dehydrogenase type 1", *Biochem. J.*, 304; pp. 289-293; (1994).
Written Opinion of the International Searching Authority for International Application No. PCT/FI2015/050928 (dated Mar. 29, 2017).
Search Report for Finnish Patent Application No. 20146149, dated Aug. 18, 2015, 3 pages.
Chinese Office Action for Application No. 201580075481.5, dated Oct. 17, 2018 (with translation).

* cited by examiner

PRODRUGS OF 17β-HSD1-INHIBITORS

FIELD OF THE INVENTION

The present invention relates to novel compounds, to their pharmaceutically acceptable salts, and to their use in therapy for inhibiting 17β-hydroxysteroid dehydrogenases. The invention further relates to pharmaceutical compositions comprising these compounds.

BACKGROUND OF THE INVENTION

17β-hydroxysteroid dehydrogenases (17β-HSDs), also known as 17-ketosteroid reductases (17-KSR) are NAD(H)- and/or NAPD(H)-dependent alcohol oxidoreductase enzymes which catalyse the last and key step in formation of all estrogens and androgens. More specifically 17β-HSDs catalyse the dehydrogenation (oxidation) of 17-hydroxysteroids into corresponding 17-ketosteroids or hydrogenation (reduction) of inactive 17-ketosteroids into corresponding active 17-hydroxysteroids.

As both estrogens and androgens have the highest affinity for their receptors in the 17β-hydroxy form, the 17β-HSD/KSRs regulate the biological activity of the sex hormones. At present, 15 human members of 17β-HSDs have been described (type 1-15). Different types of 17β-HSD/KSRs differ in their substrate and cofactor specificities. The 17KSR activities convert low-activity precursors to more potent forms while 17β-HSD activities decrease the potency of estrogens and androgens and consequently may protect tissues from excessive hormone action.

Each type of 17β-HSD has a selective substrate affinity and a distinctive, although in some cases overlapping, tissue distribution.

Type 1 17β-hydroxysteroid dehydrogenase (17β-HSD1) is most abundantly expressed in the ovarian granulosa cells of the developing follicles in ovaries and in human placenta, both being estrogen biosynthetic tissues. In addition, 17β-HSD1 is expressed in estrogen target tissues, including breast, endometrium and bone. The human 17β-HSD1 is specific to estrogenic substrates and in vivo catalyzes the reduction of estrone to estradiol.

Type 2 17β-hydroxysteroid dehydrogenase (17β-HSD2) on the other hand converts estradiol, testosterone and 5a-dihydrotestrosterone to their less active forms estrone, androstenedione and 5a-androstanedione, respectively. Due to its wide and abundant expression in number of various estrogen and androgen target tissues, such as uterus, placenta, liver and the gastrointestinal and urinary tracts, it has been suggested that type 2 enzyme protects tissues from excessive steroid actions.

Estradiol (E2) is about 10 times as potent as estrone (E1) and about 80 times as potent as estratriol (E3) in its estrogenic effect. In contrast to certain other estrogens, estradiol binds well to both estrogen receptors ERα and ERβ, and thus regulates the expression of a variety of genes.

Although both 17β-HSD1 and 17β-HSD2 are present in healthy premenopausal humans, increased ratio of 17β-HSD1 to 17-HSD2 in the tumors of postmenopausal patients with hormone-dependent breast cancer has been shown in several studies. 17HSD1 gene amplification and loss of heterozygosity of 17HSD2 allele are potential mechanisms involved to increased reductive estrogen synthesis pathway in breast tumors. Increased ratio of type 1 enzyme to type 2 enzyme results in an increased level of estradiol that then promotes the proliferation of the cancerous tissue via the estrogen receptors (ER). High levels of estrogen thus support certain cancers such as breast cancer and cancer of the uterine lining i.e. endometrial cancer and uterine cancer.

Similarly it has been suggested that 17β-HSD2 is down-regulated in endometriosis while both aromatase and 17β-HSD1 are expressed or upregulated in comparison with normal endometrium. This again results in the presence of high concentration of estradiol (E2) which drives the proliferation of the tissue. Similar mechanism has been elucidated in uterine leiomyoma (uterine fibroids) and endometrial hyperplasia.

Reduction of the endogenous estradiol concentration in affected tissues will result in reduced or impaired proliferation of 17β-estradiol cells in said tissues and may thus be utilized in prevention and treatment of malign and benign estradiol dependent pathologies. Due to the proposed involvement of 17β-estradiol in a number of malign and benign pathologies, inhibitors of 17β-hydroxysteroid dehydrogenases, that can be used to impair endogenous production of estradiol from estrone, can have therapeutic value in the prevention or the treatment of such disorders or diseases are in great demand.

Some small-molecule inhibitors of 17β-HSD1 enzyme have been identified and reviewed in Poirier D. (2003) Curr Med Chem 10: 453-77 and Poirier D. (2010) Expert Opin. Ther. Patents 20(9): 1123-1145. Further, small molecule inhibitors of 17β-HSD's have been disclosed in WO 2001/42181, WO 2003/022835, WO 2003/033487, WO 2004/046111, WO 2004/060488, WO 2004/110459, WO 2005/032527, and WO 2005/084295.

WO2004/085457 discloses steroidal compounds capable of inhibiting 17β-hydroxysteroid dehydrogenase. WO2006/003012 discloses 2-substituted D-homo-estriene derivatives suitable for the treatment of estrogen-dependent diseases that can be influenced by the inhibition of the 17β-hydroxysteroid dehydrogenase type 1. Similarly WO2006/003013 presents 2-substituted estratrienones usable for preventing and treating estrogen-dependent diseases influenced by inhibiting 17β-hydroxysteroid dehydrogenase type 1.

15-substituted estradiol analogues acting as locally active estrogens are presented in WO2004/085345. WO2006/027347 discloses 15b-substituted estradiol derivatives having selective estrogenic activity for the treatment or prevention of estrogen receptor-related diseases and physiological conditions. Further, WO2005/047303 discloses 3, 15 substituted estrone derivatives capable of inhibiting the 17β-hydroxysteroid dehydrogenase type 1.

International application WO2008/034796 relates to estratrien triazoles suitable for use in treatment and prevention of steroid hormone dependent diseases or disorders requiring the inhibition of a 17β-hydroxysteroid dehydrogenases such as 17β-HSD type 1, type 2 or type 3 enzyme. Inhibitors of 17β-HSD type 3 enzyme have been disclosed in WO99/46279.

BRIEF DESCRIPTION OF THE INVENTION

An object of the present invention is to provide novel compounds that have improved therapeutic properties useful in treating disorders and diseases associated with increased level of estradiol and/or treatable by inhibition of 17β-HSD1 enzyme. It is further an object of the present invention to provide compounds that show little or no inhibitory effect on 17β-HSD2 enzyme.

The compounds of the invention may act as prodrugs. By virtue of the nature of the masking moieties, when included in the compounds of the present invention, masked biologically active entities can delivered to the patients in need thereof. Moreover, the compounds of the invention will advantageously exhibit better solubility and resultantly better bioavailability in vivo than the corresponding naked biologically active entity.

The present invention accordingly provides novel compounds of formula (I)

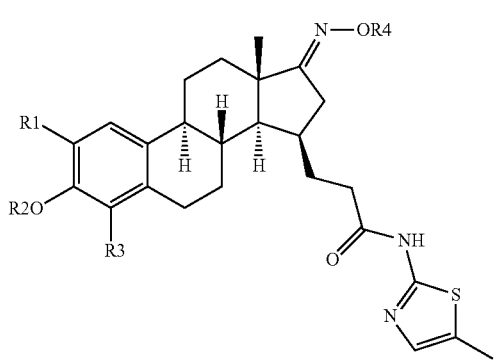

(I)

wherein R1, R2, R3 and R4 are as defined in the claims.

The invention also relates to pharmaceutical compositions comprising an effective amount of one or more compound(s) of formula (I).

Further the invention relates to a compound of formula (I) or a pharmaceutically acceptable salt thereof for use as a medicament.

The invention also relates to a compound of formula (I) or a pharmaceutically acceptable salt thereof for use in the treatment of estradiol dependent malign or benign diseases and disorders.

Finally the invention provides a method for the preparation of compounds of formula (I).

DETAILED DESCRIPTION OF THE INVENTION

Compounds of the invention contain steroidal core structure having a defined stereochemistry that is the natural configuration of estrogens.

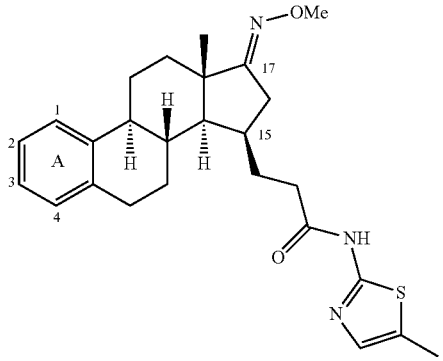

Compounds of the invention bear a methyl thiazolyl side chain at C15 in β-configuration which, together with the specific substitution pattern of the A ring, provides the inventive properties of the compounds of the present invention. Also, the C-17 carbonyl group of the native estrone core is masked as a C-17 ketimine. This particular C-17 moiety enhances the metabolic and/or inhibitory properties of the compounds of the present invention. And in particular the C-3 OH moiety of the active entity is masked with a non-toxic protecting group to advantageously alter the solubility of the compounds.

We have earlier shown that compounds disclosed in PCT/FI2014/050518, the entire contents and disclosures of which are hereby incorporated by reference, are useful in treating disorders and diseases associated with increased level of estradiol and/or treatable by inhibition of 17β-HSD1 enzyme. These compounds show little or no inhibitory effect on 17β-HSD2 enzyme.

Particular examples of such compounds disclosed in PCT/FI2014/050518 are compounds of formula (VIV)

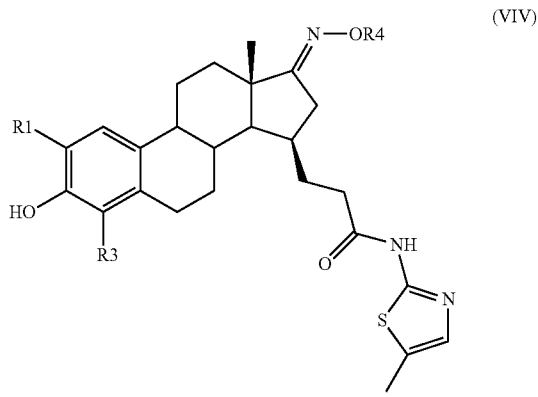

(VIV)

wherein
R1 is $C_{1-6}$-alkyl;
R3 is H or halogen; and
R4 is H or $C_{1-3}$-alkyl.

However, the compounds disclosed in PCT/FI2014/050518 are either poorly soluble or insoluble in water thus limiting routes of administration and/or drug formulation. For example for oral administration the compounds disclosed in PCT/FI2014/050518 would have to be administrated with surfactants which may cause serious side effects to some patients. Thus development of a water-soluble compounds is highly desired to improve bioavailability.

The object of the present invention is to provide compounds including a therapeutically active entity of formula (VIV). In an aspect of the present invention the compounds of the invention are water-soluble prodrug compounds. The particular water-soluble compounds can be administered orally without undesirable dissolving aids.

Compounds of the present invention convert to the substantially water-insoluble selective 17β-HSD1 inhibitory compounds following administration to a subject. The compounds of the present invention are hydrolyzed by an esterase in vivo to deliver the active ingredient. The compounds may also have biological activity as such. Accordingly the compounds of the invention may be active entities as such as well as deliver a biologically active parent molecule. The compounds of the present invention, having the structural formula (I) below, itself may show weak or strong in vitro inhibitory activity against 17β-HSD1, while the masked active entity (VIV) has strong inhibitory activity against 17β-HSD1 but show little or no inhibitory effect on 17β-HSD2.

The term "alkyl" as used herein and hereafter as such or as part of haloalkyl, perhaloalkyl or alkoxy group is an aliphatic linear, branched or cyclic, especially linear or branched, hydrocarbon group having the indicated number of carbon atoms, for example $C_{1-6}$-alkyl has 1 to 6 carbon atoms in the alkyl moiety and thus, for example, $C_{1-3}$-alkyl includes methyl, ethyl, n-propyl, isopropyl, and $C_{1-6}$-alkyl additionally includes branched and straight chain n-butyl, sec-butyl, isobutyl, tert-butyl, pentyl and hexyl.

The term "haloalkyl" as used herein and hereafter refers to any of the above alkyl groups where one or more hydrogen atoms are replaced by halogen(s): in particular I, Br, F or Cl. Examples of haloalkyl groups include without limitation chloromethyl, fluoromethyl and —$CH_2CF_3$. The term "perhaloalkyl" is understood to refer to an alkyl group, in which all the hydrogen atoms are replaced by halogen atoms. Preferred examples include trifluoromethyl (—$CF_3$) and trichloromethyl (—$CCl_3$).

The term "halogen" as used herein and hereafter by itself or as part of other groups refers to the Group VIIIa elements and includes F, Cl, Br and I.

The term "$C_{3-6}$-cycloalkyl" as used herein and hereafter refers to cycloalkyl groups having 3 to 6 carbon atoms and thus includes cyclopropyl, cyclobutyl, cyclopentyl, and cyclohexyl.

The term "alkenyl" as used herein and hereafter is an unsaturated linear or branched hydrocarbon group having at least one olefinic double bond between any two carbon atoms and having the indicated number of carbon atoms, for example $C_{2-6}$-alkenyl has 2 to 6 carbon atoms in the alkenyl moiety, such as ethenyl, propenyl, butenyl, pentenyl, and hexenyl. Examples of preferred alkenyls groups include, but are not limited to, linear alkenyl groups having a terminal double bond such as vinyl and allyl groups.

The term "optionally substituted" as used herein and hereafter in context of a phenyl group denotes phenyl that is either un-substituted or substituted independently with one or more, in particular 1, 2, or 3, substituent(s) attached at any available atom to produce a stable compound, e.g. phenyl may be substituted once with a denoted substituent attached to o-, p- or m-position of the phenyl ring. In general "substituted" refers to a substituent group as defined herein in which one or more bonds to a hydrogen atom contained therein are replaced by a bond to a non-hydrogen atom unless otherwise denoted. The substituent groups are each independently selected from the group consisting of halogen; $C_{1-4}$-alkyl, in particular methyl; OH; $C_{1-4}$-alkoxy, in particular methoxy; CN; $NO_2$; and acetoxy. Preferably said phenyl is optionally substituted with acetoxy.

"Optional" or "optionally" denotes that the subsequently described event or circumstance may but need not occur, and that the description includes instances where the event or circumstance occurs and instances in which it does not. "Comprises" or "comprising" denotes that the subsequently described set may but need not include other elements.

The expression "pharmaceutically acceptable" represents being useful in the preparation a pharmaceutical composition that is generally safe, non-toxic, and neither biologically nor otherwise undesirable, and includes being useful for both veterinary use as well as human pharmaceutical use.

The term "pharmaceutically acceptable salts" refers to salts which are known to be non-toxic and are commonly used in the pharmaceutical literature. Typically these are acid addition salts or base addition salts of the referred compounds.

The expression "acid addition salt" includes any non-toxic organic and inorganic acid addition salts that compounds of formula (I) can form. Illustrative inorganic acids, which form suitable salts, include, but are not limited to, hydrogen chloride, hydrogen bromide, sulphuric and phosphoric acids. Illustrative organic acids, which form suitable salts, include, but are not limited to, acetic acid, lactic acid, malonic acid, succinic acid, glutaric acid, fumaric acid, malic acid, tartaric acid, citric acid, ascorbic acid, maleic acid, benzoic acid, phenylacetic acid, cinnamic acid, methane sulfonic acid, salicylic acid, and the like. The term "acid addition salt" as used herein also comprises solvates which the compounds and salts thereof are able to form, such as, for example, hydrates, alcoholates, and the like. These salts also include salts useful for the chiral resolution of racemates.

The expression "base addition salt" includes any non-toxic base addition salts that the compound of formula (I) can form. Suitable base salts include, but are not limited to, those derived from inorganic bases such as aluminum, ammonium, calcium, copper, iron, lithium, magnesium, manganese, potassium, sodium, and zinc salts, in particular sodium and ammonium salts. Further examples of organic base addition salt include salts of trialkylamines, such as triethyl amine and trimethyl amine, and choline salts.

The objects of the invention may be achieved by novel compounds having formula (I)

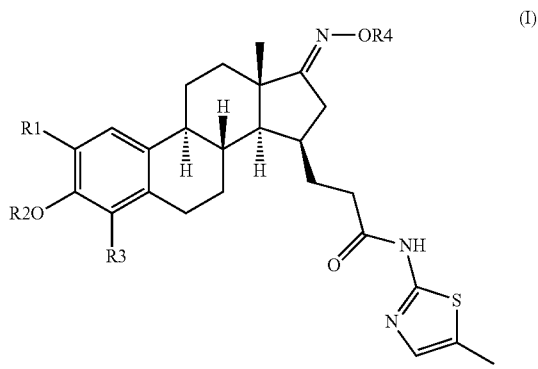

(I)

wherein

R1 $C_{1-6}$-alkyl;

R2 is selected from the group consisting of $SO_2OH$, $SO_2R''$, $SO_2N(R')_2$, $(CH_2O)_mPO(OR')_2$, COOR''', C(O)N(R')_2$, $C(O)(CH_2)_nN(R')_2$, $C(O)CH_2NR'C(O)R'$, $C(O)CH_2NR'C(O)OR''$ and $C(O)R'''$;

R3 is H or halogen; and

R4 is H or $C_{1-3}$-alkyl;

whereby

R' is H or $C_{1-6}$-alkyl, $C_{1-3}$-haloalkyl, or $C_{1-3}$-perhaloalkyl, or when part of any $N(R')_2$ both R's together with the nitrogen they are attached to may form a 5 to 6 membered aliphatic or aromatic heterocyclic ring comprising 1 or 2 heteroatoms each independently selected from N and O or a charged $N(R')_3^+$ group wherein R' is as defined above;

R'' is $C_{1-6}$-alkyl, $C_{1-3}$-haloalkyl, $C_{1-3}$-perhaloalkyl, or an optionally substituted phenyl;

R''' is $C_{1-6}$-alkyl; $C_{2-6}$-alkenyl; —$(CH_2)_n$—$C_{3-6}$-cycloalkyl; a 5 to 6 membered aliphatic or aromatic heterocyclic ring comprising 1 or 2 heteroatoms each independently selected from N and O, optionally substituted at any N atom by C(O)R' wherein R' is as defined above; or an optionally substituted phenyl;

m is 0 or 1; and n is 1 or 2 and pharmaceutically acceptable salts thereof.

In an aspect of the invention R1 is t-Bu. Compounds of formula (I) wherein R1 is t-Bu show exhibit particularly good 17β-HSD1 inhibition.

In further aspect of the invention R4 is methyl or ethyl, in particular methyl. Compounds of formula (I) wherein R4 is methyl or ethyl, in particular methyl, exhibit show little or no inhibitory effect on 17β-HSD2 enzyme.

In further aspect of the invention R3 is H.

Accordingly in a particular aspect of the present invention is provided compounds of formula (I) having formula (Ia), (Ia)

wherein
R2 is selected from the group consisting of SO$_2$OH, SO$_2$R'', SO$_2$N(R')$_2$, (CH$_2$O)$_m$PO(OR')$_2$, COOR''', C(O)N(R')$_2$, C(O)(CH$_2$)$_n$N(R')$_2$, C(O)CH$_2$NR'C(O)R', C(O)CH$_2$NR'C(O)OR'' and C(O)R''';
R3 is H or halogen; and
R4 is H or C$_{1-3}$-alkyl;
whereby
R' is H or C$_{1-6}$-alkyl, C$_{1-3}$-haloalkyl, or C$_{1-3}$-perhaloalkyl, or when part of any N(R')$_2$ both R's together with the nitrogen they are attached to may form a 5 to 6 membered aliphatic or aromatic heterocyclic ring comprising 1 or 2 heteroatoms each independently selected from N and O or a charged N(R')$_3$$^+$ group wherein R' is as defined above;
R'' is C$_{1-6}$-alkyl, C$_{1-3}$-haloalkyl, C$_{1-3}$-perhaloalkyl, or an optionally substituted phenyl;
R''' is C$_{1-6}$-alkyl; C$_{2-6}$-alkenyl; —(CH$_2$)$_n$—C$_{3-6}$-cycloalkyl; a 5 to 6 membered aliphatic or aromatic heterocyclic ring comprising 1 or 2 heteroatoms each independently selected from N and O, optionally substituted at any N atom by C(O)R' wherein R' is as defined above; or an optionally substituted phenyl;
m is 0 or 1; and
n is 1 or 2
or a pharmaceutically acceptable salt thereof.

In still further aspect of the present invention is provided compounds of formula (I) and (Ia), wherein R2 is selected from the group consisting of (CH$_2$O)$_m$PO(OR')$_2$, C(O)(CH$_2$)$_n$N(R')$_2$, C(O)CH$_2$NR'C(O)R', and C(O)CH$_2$NR'C(O)OR''. Preferred are compounds of formula (I) and (Ia) are those wherein R2 is C(O)(CH$_2$)$_n$N(R')$_2$. These compounds exhibit aqueous solubility.

Further preferred are compounds of formula (I) and (Ia), wherein R2 is (CH$_2$O)$_m$PO(OR')$_2$, wherein R' is H, C$_{1-6}$-alkyl, C$_{1-3}$-haloalkyl, or C$_{1-3}$-perhaloalkyl, and m is 0 or 1. These compounds show particularly good aqueous solubility as will be demonstrated below.

In an aspect of the present invention relates to a compound of formula (I) selected from the group consisting of:

Compound 1 Phosphoric acid mono-{(13S,15R)-2-tert-butyl-17[(E)methoxyimino]-13-methyl-15-[2-(5-methylthiazol-2-ylcarbamoyl) ethyl-7,8,9,11,12,13,14,15,16,17-decahydro-6H-cyclopenta[a]phenanthren-3-yl}ester;

Compound 2 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl(tertbutoxycarbonyl)glycinate;

Compound 3 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl glycinate;

Compound 4 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate;

Compound 5 (13S,15R)-2-(tert-butyl)-17 [(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl N-tertbutoxycarbonyl)-N-methylglycinate;

Compound 6 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl methylglycinate;

Compound 7 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl 2-morpholinoacetate;

Compound 8 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl triethylglycinate, chloride salt;

Compound 9 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl isopropylglycinate;

Compound 10 Acetic acid (13S,15R)-2-tert-butyl-13-methyl-17[(E)methoxyimino]-15-[2-(5-methyl-thiazol-2-yl-carbamoyl)-ethyl]-7,8,9,11,12,13,14,15,16,17-decahydro-6H-cyclopenta[a]phenanthren-3-yl ester;

Compound 11 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl hydrogen sulphate;

Compound 12 (13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl sulphamate;

Compound 13 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl 3-cyclopentylpropanoate Compound 14 Di-tert-butyl ((((13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)methyl) phosphate;

Compound 15 (((13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)-methyl dihydrogen phosphate;

Compound 16 tert-Butyl ((13S,15R)-2-(tert-butyl)-17 [(E)methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl) carbonate;

Compound 17 1-(tert-butyl) 2-((13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl) pyrrolidine-1,2-dicarboxylate;

Compound 18 (13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl prolinate;

and pharmaceutically acceptable salts thereof.

In a preferred aspect of the present invention relates to a compound of formula (I) selected from the group consisting of:

Compound 1 Phosphoric acid mono-{(13S,15R)-2-tert-butyl-17[(E)methoxyimino]-13-methyl-15-[2-(5-methylthiazol-2-ylcarbamoyl) ethyl-7,8,9,11,12,13,14,15,16,17-decahydro-6H-cyclopenta[a]phenanthren-3-yl}ester;

Compound 2 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl (tertbutoxycarbonyl) glycinate;

Compound 3 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl glycinate;

Compound 4 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate;

Compound 5 (13S,15R)-2-(tert-butyl)-17 [(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl N-tertbutoxycarbonyl)-N-methylglycinate;

Compound 6 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl methylglycinate;

Compound 7 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl 2-morpholinoacetate;

Compound 8 13S,15R)-2-(tert-butyl)-17[(E)methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl triethylglycinate, chloride salt;

Compound 9 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl isopropylglycinate;

Compound 14 Di-tert-butyl (((((13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)methyl) phosphate;

Compound 15 (((13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)-methyl dihydrogen phosphate;

Compound 17 1-(tert-butyl) 2-((13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl) pyrrolidine-1,2-dicarboxylate;

Compound 18 (13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl prolinate;

and pharmaceutically acceptable salts thereof.

In another aspect of the present invention relates to a compound of formula (I), selected from the group consisting of:

Compound 1 Phosphoric acid mono-{(13S,15R)-2-tert-butyl-17[(E)methoxyimino]-13-methyl-15-[2-(5-methylthiazol-2-ylcarbamoyl) ethyl-7,8,9,11,12,13,14,15,16,17-decahydro-6H-cyclopenta[a]phenanthren-3-yl}ester;

Compound 1a Phosphoric acid mono-{(13S,15R)-2-tert-butyl-17[(E)-methoxyimino]-13-methyl-15-[2-(5-methylthiazol-2-ylcarbamoyl) ethyl-7,8,9,11,12,13,14,15,16,17-decahydro-6H-cyclopenta[a]phenanthren-3-yl}ester disodium salt;

Compound 2 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl (tertbutoxycarbonyl) glycinate;

Compound 3a (13S,15R)-2-(tert-butyl)-17[(E)methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl glycinate trifluoroacetate;

Compound 3b (13S,15R)-2-(tert-butyl)-17[(E)methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl glycinate hydrochloride;

Compound 4 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate;

Compound 4a (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate hydrochloride;

Compound 5 (13S,15R)-2-(tert-butyl)-17 [(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl N-tertbutoxycarbonyl)-N-methylglycinate;

Compound 6a (13S,15R)-2-(tert-butyl)-17 [(E)methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl methylglycinate hydrochloride;

Compound 7 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl 2-morpholinoacetate;

Compound 8 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl triethylglycinate, chloride salt;

Compound 9 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl isopropylglycinate;

Compound 9a (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl isopropylglycinate hydrochloride;

Compound 10 Acetic acid (13S,15R)-2-tert-butyl-13-methyl-17[(E)methoxyimino]-15-[2-(5-methyl-thiazol-2-yl-carbamoyl)-ethyl]-7,8,9,11,12,13,14,15,16,17-decahydro-6H-cyclopenta[a]phenanthren-3-yl ester;

Compound 11a (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl hydrogen sulphate, triethylammonium salt;

Compound 12 (13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl sulphamate;

Compound 13 (13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl 3-cyclopentylpropanoate Compound 14 Di-tert-butyl ((((13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)methyl) phosphate;

Compound 15 (((13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)methyl dihydrogen phosphate;

Compound 15a (((13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)methyl dihydrogen phosphate disodium salt;

Compound 16 tert-Butyl ((13S,15R)-2-(tert-butyl)-17[(E)methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl) carbonate;

Compound 18a (13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl prolinate 2,2,2-trifluoroacetate; and Compound 18b (13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl prolinate hydrochloride.

Examples of the Therapeutically Active Entities of Formula (VIV)

Representative examples of the active species liberated by the compounds of formula (I) are shown in Table 1.

TABLE 1

VIV-1

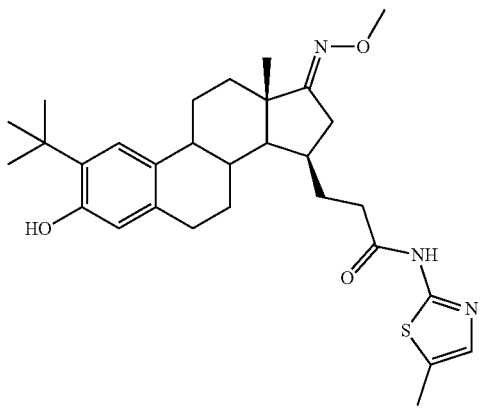 [SMILES: CO/N=C1\C[C@@H](CCC(=O)Nc2ncc(C)s2)C2C3CCc4cc(O)c(C(C)(C)C)cc4C3CC[C@]12C]

TABLE 1-continued

VIV-2

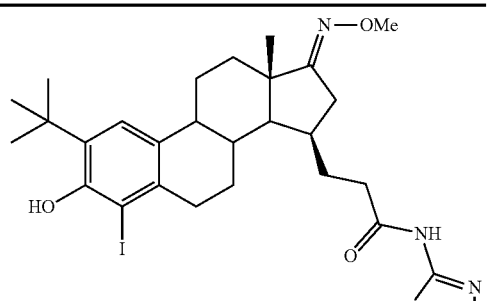

VIV-3

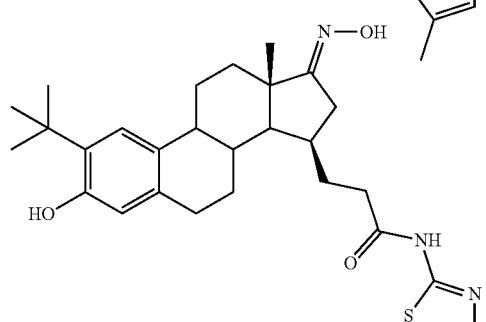

VIV-4

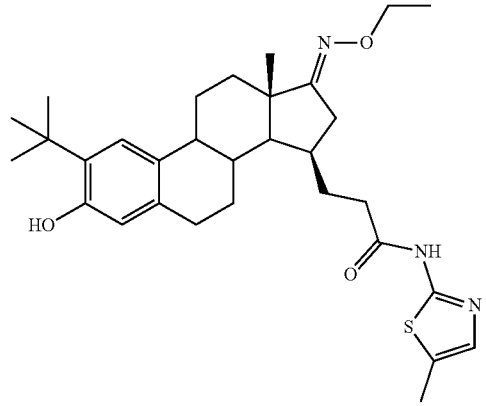 [SMILES: CCO/N=C1\C[C@@H](CCC(=O)Nc2ncc(C)s2)C2C3CCc4cc(O)c(C(C)(C)C)cc4C3CC[C@]12C]

Examples of the Invention

Representative examples of compounds of formula (I) are shown in Table 2.

TABLE 2

Examples of compounds of formula (I)

1

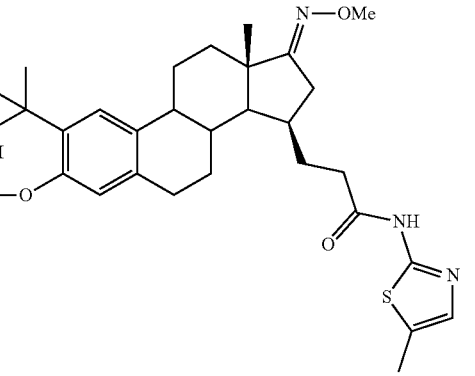

TABLE 2-continued
Examples of compounds of formula (I)
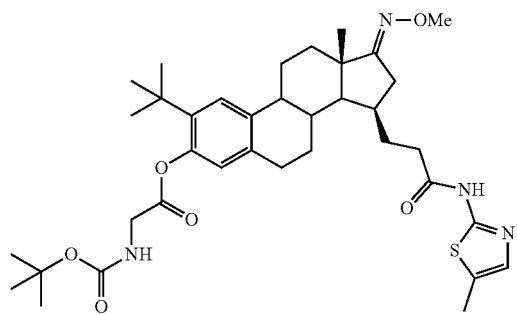 [SMILES: CO/N=C1\C[C@@H](CCC(=O)Nc2ncc(C)s2)C2C3CCc4cc(OC(=O)CNC(=O)OC(C)(C)C)c(C(C)(C)C)cc4C3CC[C@]12C]
2
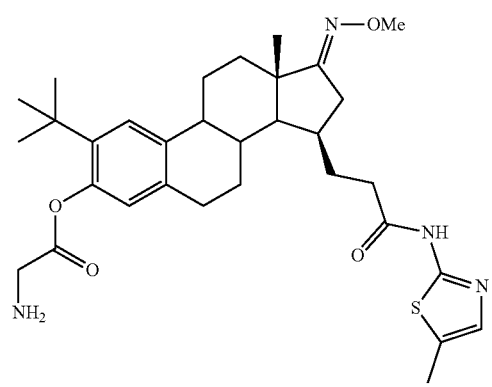 [SMILES: CO/N=C1\C[C@@H](CCC(=O)Nc2ncc(C)s2)C2C3CCc4cc(OC(=O)CN)c(C(C)(C)C)cc4C3CC[C@]12C]
3
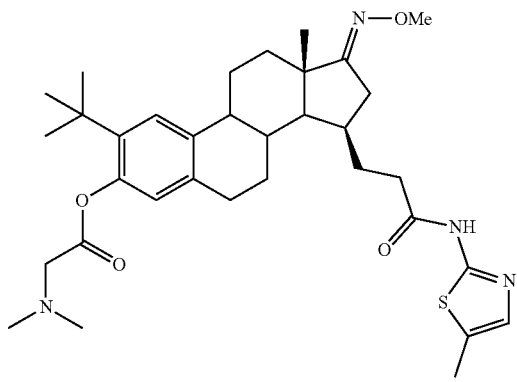 [SMILES: CO/N=C1\C[C@@H](CCC(=O)Nc2ncc(C)s2)C2C3CCc4cc(OC(=O)CN(C)C)c(C(C)(C)C)cc4C3CC[C@]12C]
4
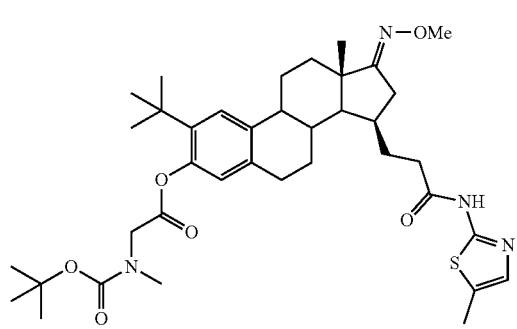 [SMILES: CO/N=C1\C[C@@H](CCC(=O)Nc2ncc(C)s2)C2C3CCc4cc(OC(=O)CN(C)C(=O)OC(C)(C)C)c(C(C)(C)C)cc4C3CC[C@]12C]
5
TABLE 2-continued
Examples of compounds of formula (I)
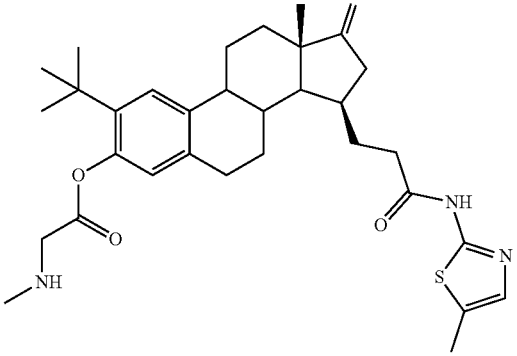
6
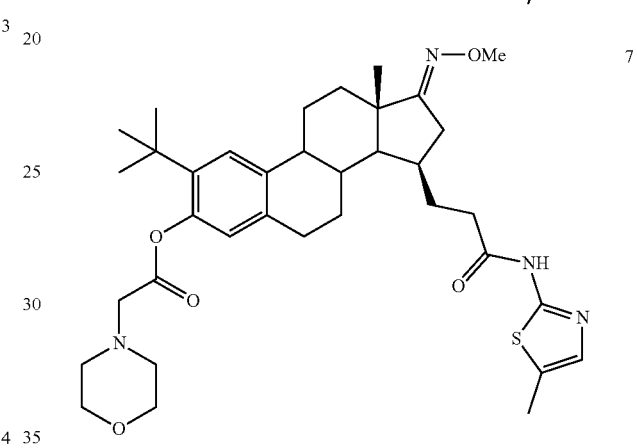
7
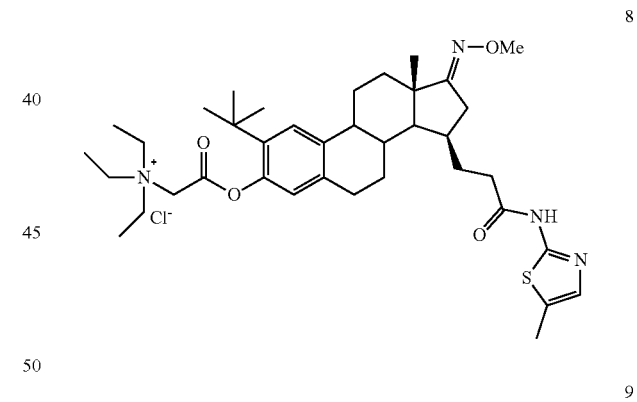
8
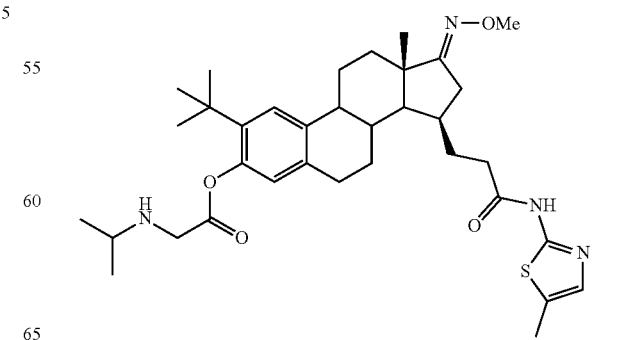
9

TABLE 2-continued
Examples of compounds of formula (I)
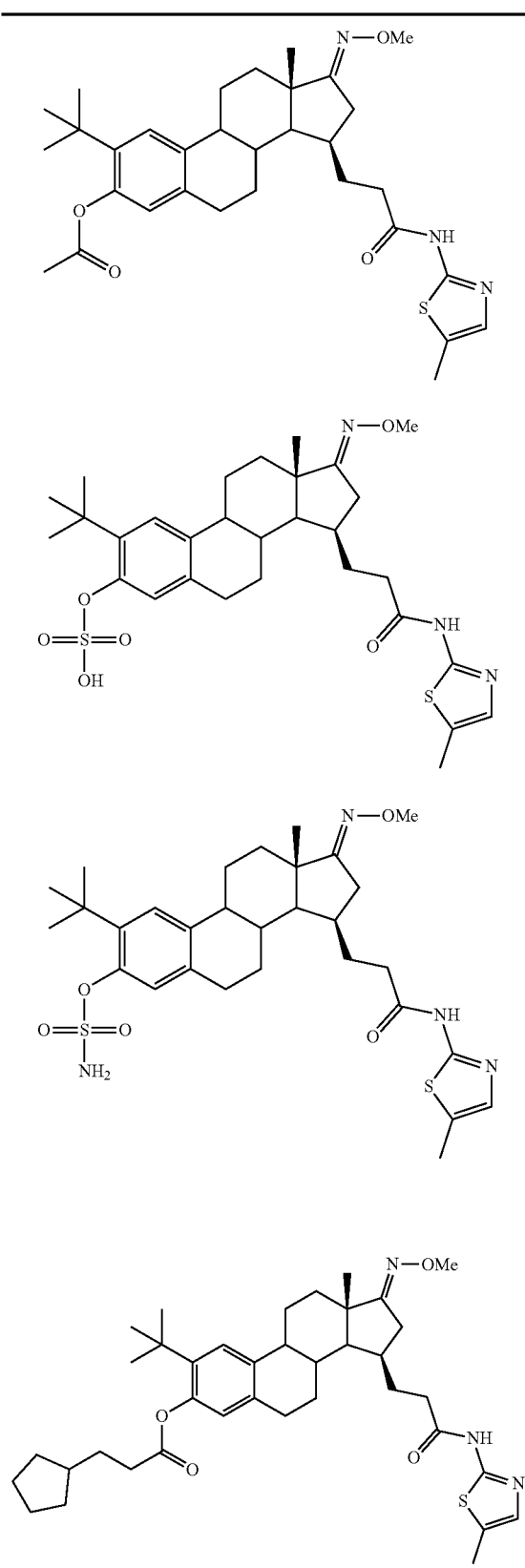
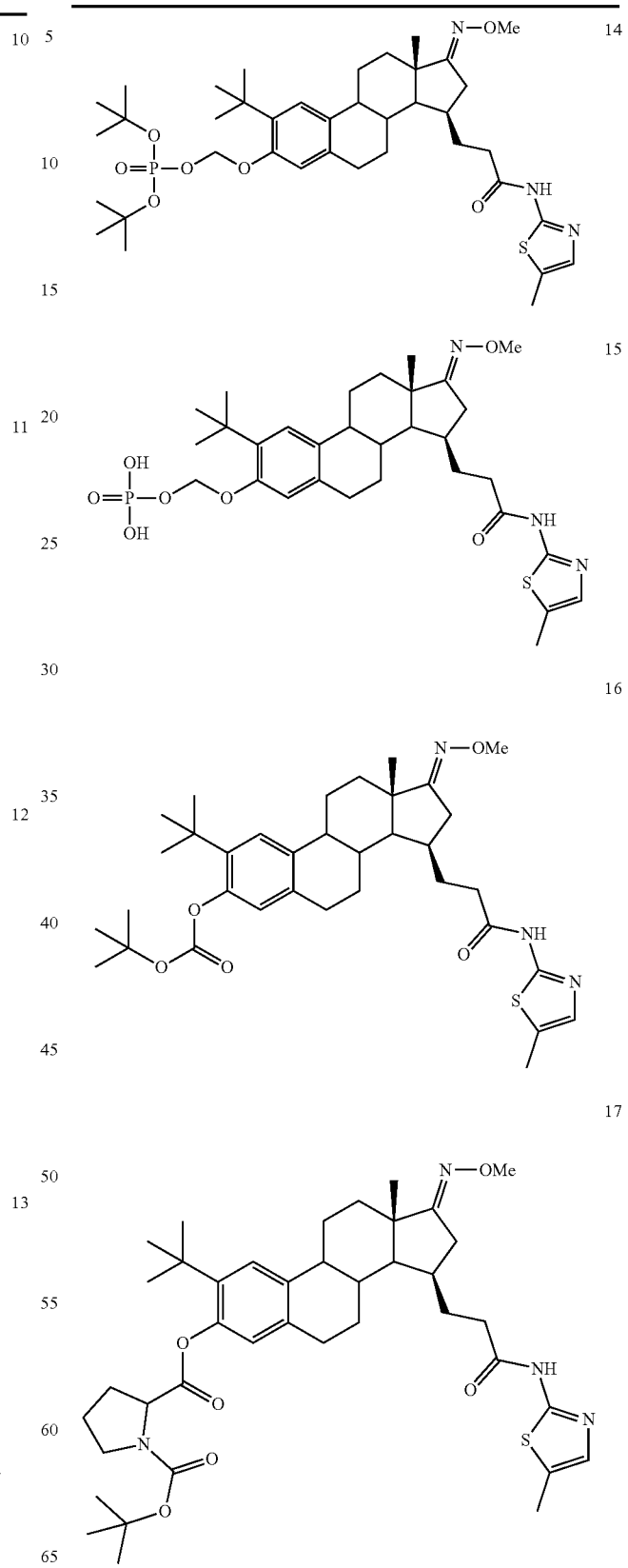

TABLE 2-continued

Examples of compounds of formula (I)

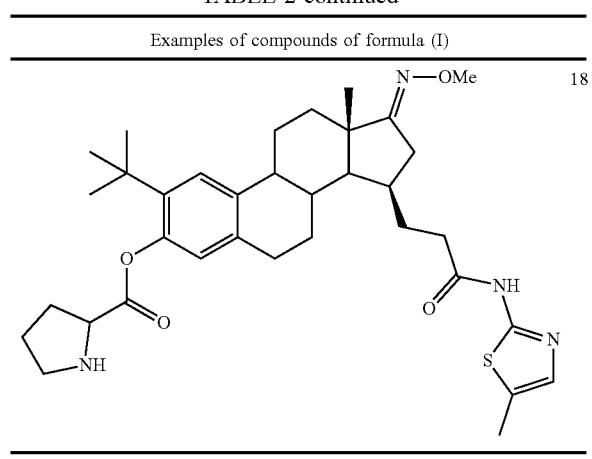

18

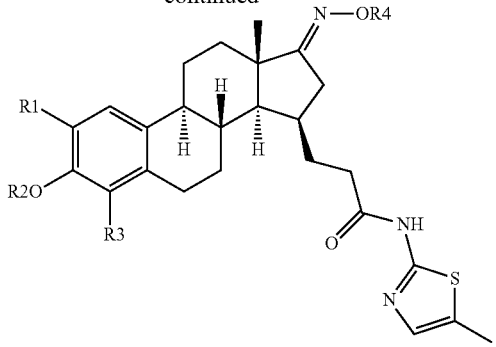

General Preparation Methods

Compounds of the present invention may be prepared by methods known in the art. The following examples illustrate the preparation of compounds of formula (I).

General Information

Commercial grade reagents and solvents were used without further purification. Thin-layer chromatography (TLC) was performed on Merck-plates; pre-coated aluminium sheets. Visualization of plates was done the following techniques: 1) ultraviolet illumination (254 nm), 2) dipping the plate into anisaldehyde or vanilline solution followed by heating. 1H-NMR spectra were measured with a Bruker DPX (200 MHz) spectrometer with the solvent as indicated.

Compounds of the invention may be prepared from the corresponding C-17 carbonyl derivatives wherein R2 is H, followed by required derivatization of the R2 with an alkyl group and modification of the C3-OH group.

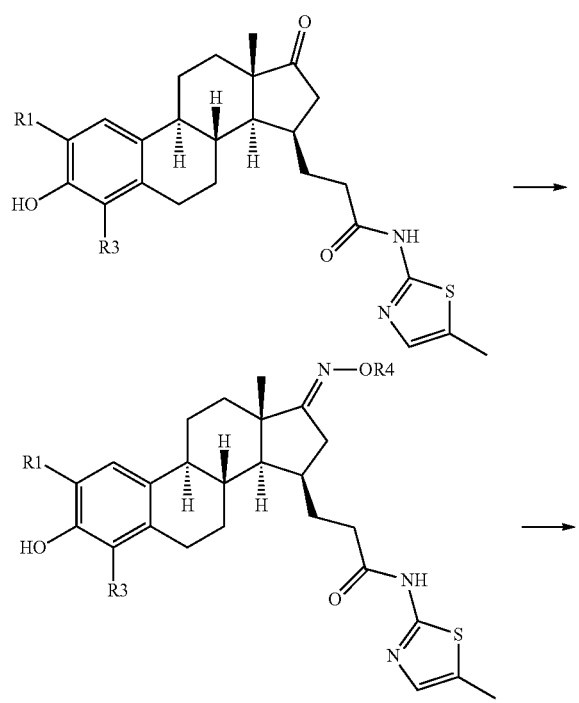

Preparation of Synthesis Starting Materials and Precursors

Compound VII

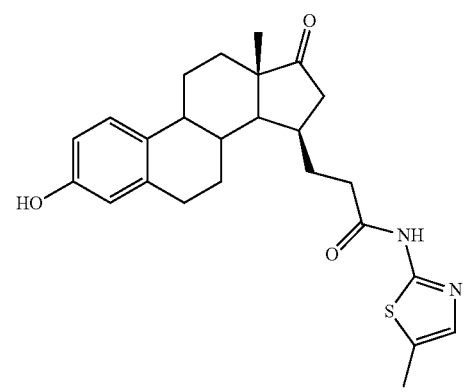 [SMILES: Cc1cnc(NC(=O)CC[C@@H]2CC(=O)[C@@]3(C)CCC4c5ccc(O)cc5CCC4C23)s1]

Compound VII may be synthesized as disclosed in Messinger et al. Mol Cell Endocrinol. 2009 (301) 216-224. The detailed synthesis of compound VII starting from estrone has been described in the Solvay Pharmaceuticals' PCT applications WO2005/047303 and WO2006/125800.

Benzyl-C15-C16-dehydroestrone II was prepared in five steps from estrone according to previously described methods. The compound II was treated with an allylic Grignard reagent in the presence of cuprous iodide and lithium chloride in temperature −78° C. Hydroboration by borane tetrahydrofuran complex at room temperature to compound III and following hydrogen peroxide oxidation in alkaline conditions produced diol IV in over 90% yields. Jones oxidation in acetone-water afforded acid V, which was debenzylated by hydrogenation to compound VI by using Pd/C as a catalyst. The final step was the amide formation affording the β-thiazole VII.

The synthesis of the key precursor i.e. the phenolic thiazole VII from estrone is shown below.

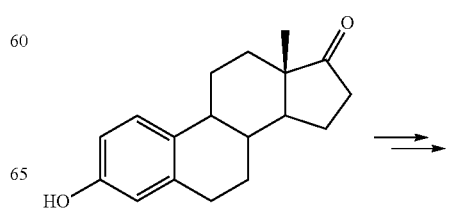

-continued

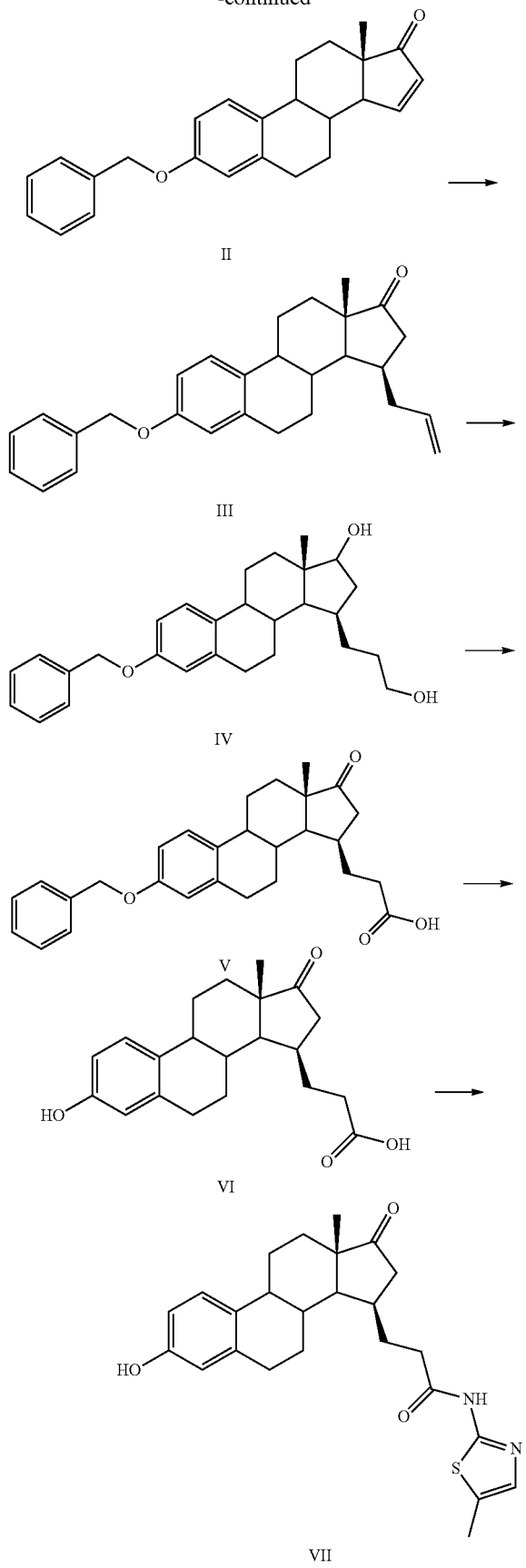

Compound VIII-1

3-((13S,15R)-2-(tert-butyl)-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide To a stirred suspension of the compound VII (2.0 g, 100 mol-%) in dry dichloromethane, tert-butanol (1.5 ml) and boron trifluoride diethyl etherate (3.2 ml) were added at rt and the reaction was followed by TLC. The mixture was stirred overnight at rt and additional amount of boron trifluoride diethyl etherate (1 ml) and tert-butanol (500 µl) were added. The resulting orange solution was stirred for 3 hours before water (40 ml) and DCM (40 ml) were added carefully. The layers were separated and the aqueous layer was extracted with DCM (3×30 ml). The combined organic layers were washed with water (3×30 ml), saturated aqueous NaHCO$_3$ (30 ml) and brine (3×30 ml). The solvents were evaporated and the precipitate was washed with heptane affording 1.8 g of the product VIII-1 (yield 80%).

$^1$H-NMR (DMSO-d$_6$): 0.97 (s, 3H), 1.2-1.45 (m, 12H), 1.5-2.4 (m, 16H), 2.6-2.95 (m, 2H), 6.47 (s, 1H), 7.01 (s, 1H), 7.11 (s, 1H), 8.97 (s, 1H), 11.92 (s, 1H, —NH). MS m/z (TOF ES+): 517 (M+Na).

Synthesis of C-17 (alkyl)oximes

General Method for the Preparation of C-17 Methyl Oximes:

Ketone (0.3 mmol) was dissolved in a mixture of ethanol (3 ml) and THF (2 ml) under nitrogen atmosphere. Pyridine (1.5 mmol) and methoxylamine hydrochloride (0.9 mmol) were added to this solution. The reaction mixture was refluxed for 1-2 h. Solvents were evaporated. Water was added and the product was either filtered or extracted with ethyl acetate, washed with dilute hydrochloric acid and finally with water. Oximes were purified further by flash-chromatography if required.

Compound VIV-1

3-{(13S,15R)-2-tert-Butyl-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl) propanamide

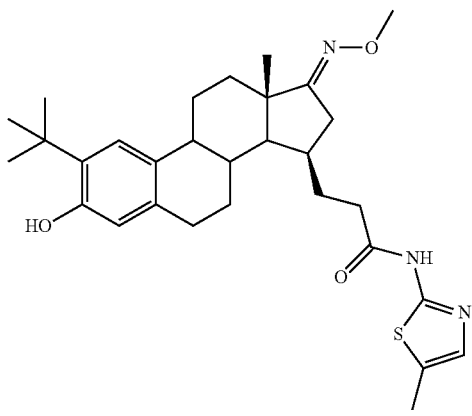 [SMILES: CO/N=C1\C[C@@H](CCC(=O)Nc2ncc(C)s2)C2C3CCc4cc(O)c(C(C)(C)C)cc4C3CC[C@]12C]

Prepared by the method as described the preparation of C-17 methyl oximes using compound VIII-1 as a starting material to provide VIV in quantitative yield.

$^1$H-NMR (CDCl$_3$+MeOH-d$_4$): 1.09 (s, 3H), 1.3-2.9 (m, 33H), 3.85 (s, 3H), 6.43 (s, 1H) 7.07 (s, 1H), 7.17 (s, 1H), 12.34 (br, 1H). MS m/z (TOF ES+): 546 (M+Na).

Compound VIV-2

3-((13S,15R,E)-2-(tert-butyl)-3-hydroxy-4-iodo-17-(methoxyimino)-13-methyl-7,8,9,11,12,13,14,15,16,17-decahydro-6H-cyclopenta[a]phenanthren-15-yl)-N-(5-methylthiazol-2 yl)propanamide

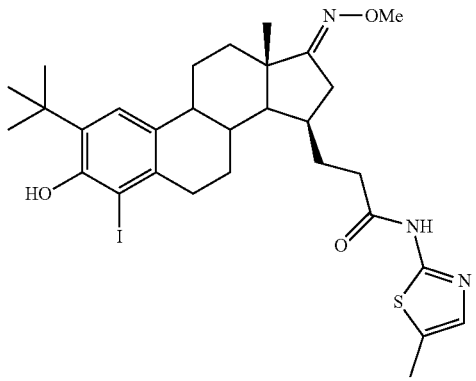 [SMILES: CO/N=C1\C[C@@H](CCC(=O)Nc2ncc(C)s2)C2C3CCc4c(cc(C(C)(C)C)c(O)c4I)C3CC[C@]12C]

The compound VIV-1 (100 mg, 0.191 mmol, 100 mol-%) and p-TsOH (33 mg, 100 mol-%) were dissolved in dry ACN (2 ml) and stirred for 15 min at rt. N-iodosuccinimide (52 mg, 0.229 mmol, 120 mol-%) was added in portions. Reaction was stirred at rt for 2.5 hours and additional amount of N-iodosuccinimide (24 mol-%) was added. Stirring was continued overnight at rt. Water was added (5 ml) and 10% Na$_2$CO$_3$ was added until pH 8. Product was extracted in EtOAc (3×10 ml). Combined organic layers were washed with 10% Na$_2$SO$_3$, water and brine and dried with Na$_2$SO$_4$. Solvent was evaporated. Crude product (123 mg) was purified with flash chromatography. The amount of the compound VIV-2 was 80 mg.

$^1$H-NMR (DMSO-d$_6$): 1.02 (s, 3H), 1.33 (s, 9H), 1.20-2.80 (m, 21H), 3.73 (s, 3H), 7.11 (s, 1H), 7.14 (s, 1H), 7.97 (s, 1H), 11.90 (br s, 1H).

Compound VIV-3

3-{(13S,15R)-2-tert-Butyl-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

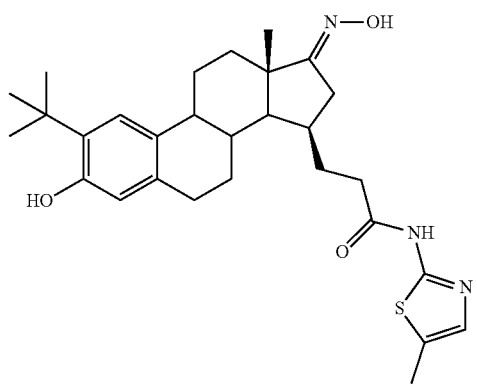 [SMILES: Cc1cnc(NC(=O)CC[C@@H]2C/C(=N\O)[C@@]3(C)CCC4c5cc(C(C)(C)C)c(O)cc5CCC4C23)s1]

Prepared using the general method above, using the compound VIII-1 as a starting material and hydroxylamine hydrochloride as the reagent, in 95% yield.

$^1$H-NMR (CDCl$_3$+MeOH-d$_4$): 1.11 (s, 3H), 1.3-3.1 (m, 34H), 6.46 (s, 1H), 7.05 (s, 1H,), 7.15 (s, 1H). MS m/z (TOF ES+): 532 (M+Na).

Compound VIV-4

3-{(13S,15R)-2-tert-Butyl-17-[(E)-ethoxyimino]-3-hydroxyl-13-methyl-7,8,9,11,12,13,14,15,16,17-decahydro-6H-cyclopenta[a]phenanthren-15-yl}-N-(5-methylthiazol-2-yl)propanamide

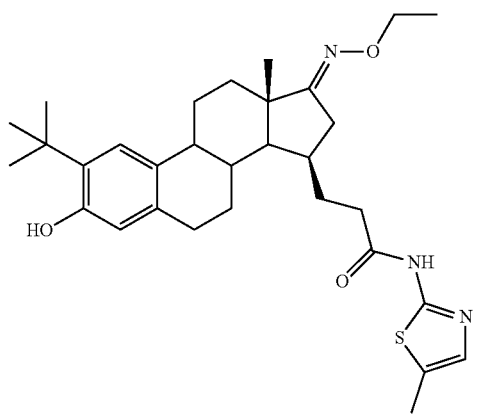 [SMILES: CCO/N=C1\C[C@@H](CCC(=O)Nc2ncc(C)s2)C2C3CCc4cc(O)c(C(C)(C)C)cc4C3CC[C@]12C]

To a suspension of VIII-1 (700 mg, 100 mol-%) and EtOH (abs.) (30 ml) was added ethyl hydroxylamine hydrochloride (670 mg, 500 mol-%) followed by pyridine (1.52 g, 1200 mol-%). The resulting solution was refluxed 3 hours and the solvent was evaporated. Water was added to the residue. The aqueous layer was extracted with EtOAc. The combined organic layers were washed with water and brine, dried over $Na_2SO_4$, filtered and evaporated. The crude product was triturated with heptane. The yield of the product was 87%.

$^1$H-NMR (DMSO-$d_6$): 1.03 (s, 3H), 1.17 (t, 3H), 1.31 (s, 9H), 1.2-2.8 (m, 18H), 2.33 (s, 3H), 3.99 (q, 2H), 6.46 (s, 1H), 7.00 (s, 1H), 7.11 (s, 1H), 8.97 (s, 1H), 11.91 (s, 1H). MS m/z (TOF ES+): 560 (M+Na), 538 (M+1).

Synthesis of C-3 Derivatives

Compound 1

Phosphoric acid mono-{(13S,15R)-2-tert-butyl-17 [(E)-methoxyimino]-13-methyl-15-[2-(5-methylthi- azol-2-ylcarbamoyl) ethyl-7,8,9,11,12,13,14,15,16, 17-decahydro-6H-cyclopenta[a]phenanthren-3- yl}ester

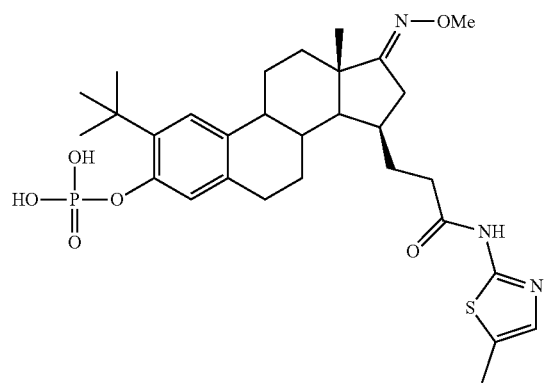 [SMILES: CO/N=C1\C[C@@H](CCC(=O)Nc2ncc(C)s2)C2C3CCc4cc(OP(=O)(O)O)c(C(C)(C)C)cc4C3CC[C@]12C]

VIV-1 (5.0 g, 100 mol-%) was dissolved in dry THF (75 ml). Pyridine (800 mol-%) was added followed by phosphorous oxychloride (800 mol-%) addition as dropwise. The solution was stirred at rt under nitrogen overnight until the reaction was completed. Next day, the solution was cooled and 200 ml of water was carefully added. Stirring was continued overnight. THF was evaporated. The precipitate solution after THF evaporation was diluted with water (~200 ml), 6N HCl-solution (~20 ml) was added until white phosphate precipitation was completed. The solid material was filtered and washed carefully with large amount of water until the filtrate was neutral. The crude product was co-evaporated with toluene and ethanol. The phosphate was carefully dried in vacuum. The yield of 1 was 2.6 g; the yield 90%.

$^1$H NMR (200 MHz, DMSO-$d_6$) δ ppm 1.04 (s, 3H), 1.31 (s, 9H), 1.48-2.90 (m, 23H), 3.73 (s, 3H), 7.11-7.15 (s+d, 3H). 11.92 (br s, 1H). $^{31}$P-NMR (DMSO-d6): −7.04. MS m/z (TOF ES+): 604 (M+H).

Compound 1a

Phosphoric acid mono-{(13S,15R)-2-tert-butyl-17 [(E)-methoxyimino]-13-methyl-15-[2-(5-methylthi- azol-2-ylcarbamoyl) ethyl-7,8,9,11,12,13,14,15,16, 17-decahydro-6H-cyclopenta[a]phenanthren-3- yl}ester disodium salt

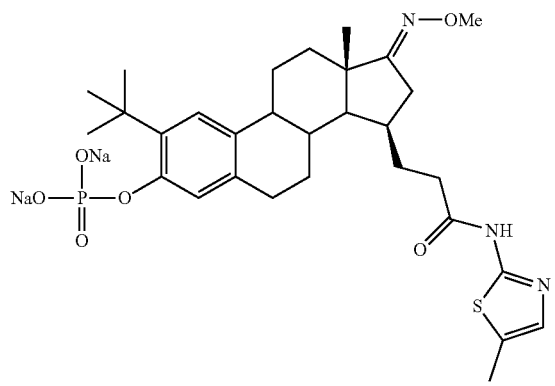

Dried 1 (2.2 g, 3.6 mmol) was dissolved in abs. ethanol (35 ml) and then filtered solution of NaOH (400 mol-%) in abs. ethanol (5 ml) was added. After stirring at rt for two hours under nitrogen, the solvents were evaporated. The precipitate was washed several times with $Et_2O$ and $Et_2O$:EtOH (4:1). The yield of 1a was 2.31 g; the yield 98%.

$^1$H NMR (200 MHz, DMSO-$d_6$) δ ppm 1.11 (s, 3H), 1.43 (s, 9H), 1.60-2.95 (m, 22H), 3.79 (s, 3H), 7.05 (d, 2H), 7.49 (s, 1H). $^{31}$P-NMR (MeOH-$d_4$): −0.41. MS m/z (TOF ES+): 604 [(M-2Na)+H]+.

Compound 2

(13S,15R)-2-(tert-butyl)-17[(E)-methoxyimino]-13- methyl-15-(3-((5-methylthiazol-2-yl)amino)-3-oxo- propyl)-7,8,9,11,12,13,14,15,16,17-decahydro-6H- cyclopenta[a]phenanthren-3-yl (tert-butoxycarbonyl) glycinate

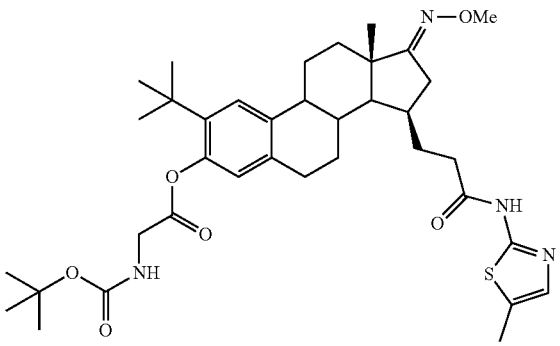 [SMILES: CO/N=C1\C[C@@H](CCC(=O)Nc2ncc(C)s2)C2C3CCc4cc(OC(=O)CNC(=O)OC(C)(C)C)c(C(C)(C)C)cc4C3CC[C@]12C]

VIV-1 (500 mg, 0.95 mmol, 100 mol-%) was dissolved in dry DCM (10 ml) at rt. Pyridine (154 µl, 1.91 mmol, 200 mol-%), BOC-glysine (184 mg, 1.05 mmol, 110 mol-%) and DCC (236 mg, 1.15 mmol, 120 mol-%) were added. Reaction was stirred under nitrogen atmosphere at rt for 3 hours. Additional amount of DCC (59 mg, 30 mol-%) was added and stirring continued overnight. Still another additional amount of BOC-glycine (184 mg, 110 mol-%) and DCC (177 mg, 90 mol-%) were added and stirring continued for 7 hours. DHU was filtered off and washed with DCM. Water (30 ml) was added and layers separated. Water layer was washed with DCM (3×20 ml). Combined organic layers were washed with 1 N HCl (5×20 ml), water (3×30 ml) and brine (2×30 ml) and dried with Na$_2$SO$_4$. The crude product (1.0 g) was purified by flash chromatography using an eluent DCM:MeOH 99:1. Amount of the product was 670 mg.

$^1$H NMR (200 MHz, DMSO-d$_6$) δ ppm 1.05 (s, 3H), 1.26 (s, 9H), 1.39 (s, 9H), 1.10-2.90 (m, 22H), 3.73 (s, 3H), 3.95-3.98 (m, 2H), 6.68 (s, 1H), 7.11 (s, 1H), 7.23 (s, 1H), 11.90 (br s, 1H).

Compound 3a (13S,15R)-2-(tert-butyl)-17[(E)-methoxyimino]-13-methyl-15-(3-((5-methylthiazol-2-yl)amino)-3-oxo-propyl)-7,8,9,11,12,13,14,15,16,17-decahydro-6H-cyclopenta[a]phenanthren-3-yl glycinate trifluoroacetate

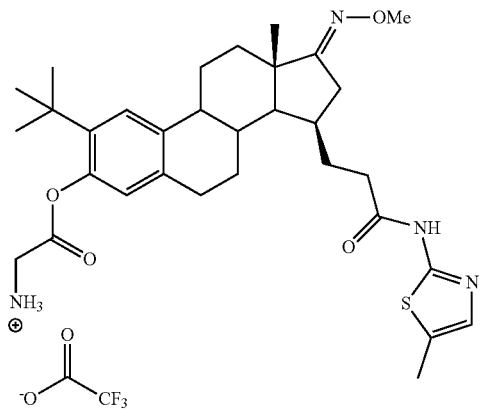

2 (450 mg) was dissolved in dry DCM (6 ml). TFA (1.2 ml) was carefully added under nitrogen atmosphere to ice cold reaction mixture. Reaction was stirred at rt for 1.5 h. Solvent was evaporated and co-evaporation with toluene was done twice. Crude product was triturated with Et$_2$O (5 ml). Precipitate was filtered and washed with Et$_2$O (2×2 ml) yielding 400 mg of the product.

$^1$H NMR (200 MHz, DMSO-d$_6$) δ ppm 1.06 (s, 3H), 1.28 (s, 9H), 1.10-2.90 (m, 21H), 3.74 (s, 3H), 4.19 (m, 2H), 6.76 (s, 1H), 7.12 (s, 1H), 7.28 (s, 1H), 8.42 (br s, 2H), 11.92 (br s, 1H).

Compound 3b (13S,15R)-2-(tert-butyl)-17[(E)-methoxyimino]-13-methyl-15-(3-((5-methylthiazol-2-yl)amino)-3-oxo-propyl)-7,8,9,11,12,13,14,15,16,17-decahydro-6H-cyclopenta[a]phenanthren-3-yl glycinate hydrochloride

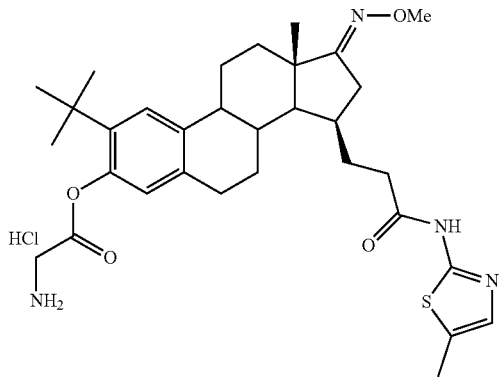 [SMILES: Cl ; CO/N=C1\C[C@@H](CCC(=O)Nc2ncc(C)s2)C2C3CCc4cc(OC(=O)CN)c(C(C)(C)C)cc4C3CC[C@]12C]

2 (300 mg, 0.52 mmol) was dissolved in abs. EtOH (10 ml) containing 20 drops of MeOH. 2M HCl (430 μl) was added under nitrogen atmosphere and reaction stirred at rt for 1.5 hours. Solvents were evaporated and co-evaporated with toluene. The crude product was triturated with EtOAc (3×1 ml), filtered and washed with EtOAc (1 ml). The amount of the product was 160 mg.

$^1$H NMR (200 MHz, DMSO-d$_6$) δ ppm 1.06 (s, 3H), 1.28 (s, 9H), 1.10-2.90 (m, 21H), 3.74 (s, 3H), 4.17 (m, 2H), 6.77 (s, 1H), 7.12 (s, 1H), 7.27 (s, 1H), 8.53 (br s, 2H), 11.93 (br s, 1H). MS m/z (TOF ES+): 603 (−HCl+Na), 581 (−HCl; M+H).

Compound 4

(13S,15R)-2-(tert-butyl)-17[(E)-methoxyimino]-13-methyl-15-(3-((5-methylthiazol-2-yl)amino)-3-oxo-propyl)-7,8,9,11,12,13,14,15,16,17-decahydro-6H-cyclopenta[a]phenanthren-3-yl dimethylglycinate

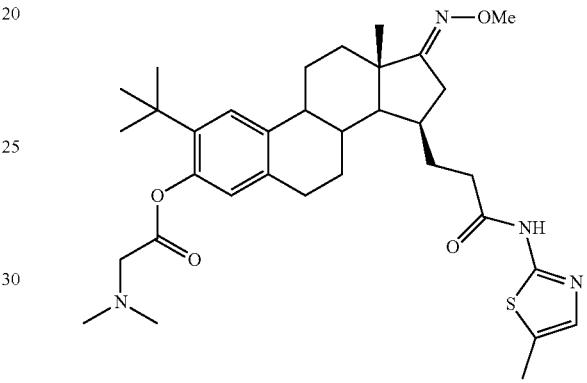

4 was prepared by using the DCC-method described for the compound 2 using VIV-1 as a starting material with addition of DMAP (30 mol-%). The reaction mixture was treated with oxalic acid and the precipitated DHU was filtered off. The product was isolated after extraction described for 2 in a quantitative yield.

$^1$H NMR (200 MHz, DMSO-d$_6$) δ ppm 1.04 (s, 3H), 1.22 (s, 9H), 1.40-2.90 (m, 27H), 3.46 (s, 2H), 3.72 (s, 3H), 6.70 (s, 1H), 7.09 (s, 1H), 7.10 (s, 1H), 11.89 (br s, 1H).

Compound 4a (13S,15R)-2-(tert-butyl)-17[(E)-methoxyimino]-13-methyl-15-(3-((5-methylthiazol-2-yl)amino)-3-oxo-propyl)-7,8,9,11,12,13,14,15,16,17-decahydro-6H-cyclopenta[a]phenanthren-3-yl dimethylglycinate hydrochloride

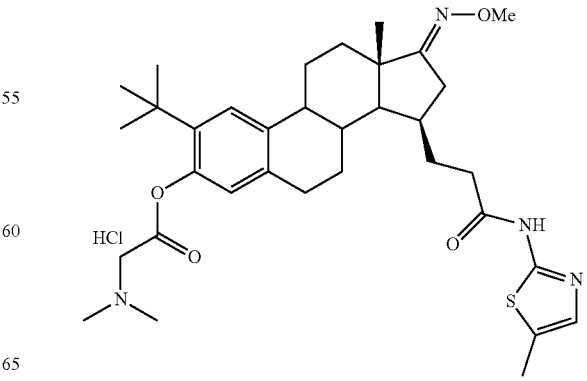

Dimethylglycine derivative 4 (2.9 g, 4.8 mmol) was dissolved in EtOAc (20 ml). Conc. HCl (1.5 ml) in EtOAc (10 ml) was added dropwise under nitrogen atmosphere to reaction mixture, and stirred for 10 minutes at rt. The solvent was evaporated and co-evaporated with toluene. The crude product was triturated with EtOAc (3×1 ml), filtered and washed several times with small amounts of EtOAc. The amount of the product was 2.53 g; the yield 82%.

¹H NMR (200 MHz, DMSO-d₆) δ ppm 1.05 (s, 3H), 1.27 (s, 9H), 1.48-2.45 (m, 18H), 2.60-2.82 (m, 3H), 2.92 (s, 6H), 3.78 (s, 3H), 4.59 (m, 2H), 6.89 (s, 1H), 7.12 (s, 1H), 7.27 (s, 1H), 10.70 (br, 1H), 11.98 (br s, 1H). MS m/z (TOF ES+): 609 [(M−HCl)+H]+

Compound 5

(13S,15R)-2-(tert-butyl)-17[(E)-methoxyimino]-13-methyl-15-(3-((5-methylthiazol-2-yl)amino)-3-oxo-propyl)-7,8,9,11,12,13,14,15,16,17-decahydro-6H-cyclopenta[a]phenanthren-3-yl N-tert-butoxycarbonyl-N-methylglycinate

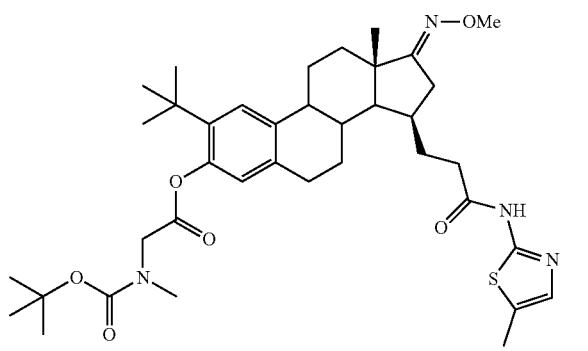 [SMILES: CO/N=C1\C[C@@H](CCC(=O)Nc2ncc(C)s2)C2C3CCc4cc(OC(=O)CN(C)C(=O)OC(C)(C)C)c(C(C)(C)C)cc4C3CC[C@]12C]

5 was prepared by using the DCC-method described for the compound 2 using VIV-1 as a starting material with addition of DMAP (30 mol-%). The reaction mixture was treated with oxalic acid and the precipitated DHU was filtered off. The product was isolated after extraction I in 74% yield.

¹H-NMR (DMSO-d₆): 1.04 (s, 3H), 1.26 (s, 9H), 1.37 (s, 3H), 1.47-2.93 (m, 22H), 3.73 (s, 3H), 4.28 (d, 2H), 6.74 (s, 1H), 7.10 (s, 1H), 7.24 (s, 1H), 11.90 (br s, 1H).

Compound 6a (13S,15R)-2-(tert-butyl)-17 [(E)-methoxyimino]-13-methyl-15-(3-((5-methylthiazol-2-yl)amino)-3-oxo-propyl)-7,8,9,11,12,13,14,15,16,17-decahydro-6H-cyclopenta[a]phenanthren-3-yl methylglycinate hydrochloride

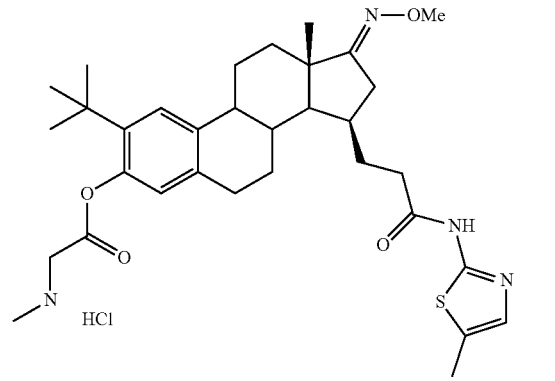 [SMILES: CNCC(=O)Oc1cc2c(cc1C(C)(C)C)C1CC[C@]3(C)/C(=N/OC)C[C@@H](CCC(=O)Nc4ncc(C)s4)C3C1CC2 ; Cl]

Prepared according the method used for the compound 3b by using HCl-EtOAc solution for hydrochloride preparation in 73% yield.

¹H NMR (200 MHz, DMSO-d₆) δ ppm 1.05 (s, 3H), 1.27 (s, 9H), 1.60-2.45 (m, 21H), 3.73 (s, 3H), 4.01 (m, 2H), 4.32 (br s, 2H), 6.80 (s, 1H), 7.12 (s, 1H), 7.27 (s, 1H), 9.44 (br s, 1H), 11.96 (br s, 1H).

Synthesis of C3 C(O)(CH₂)N(R')₂-Derivatives

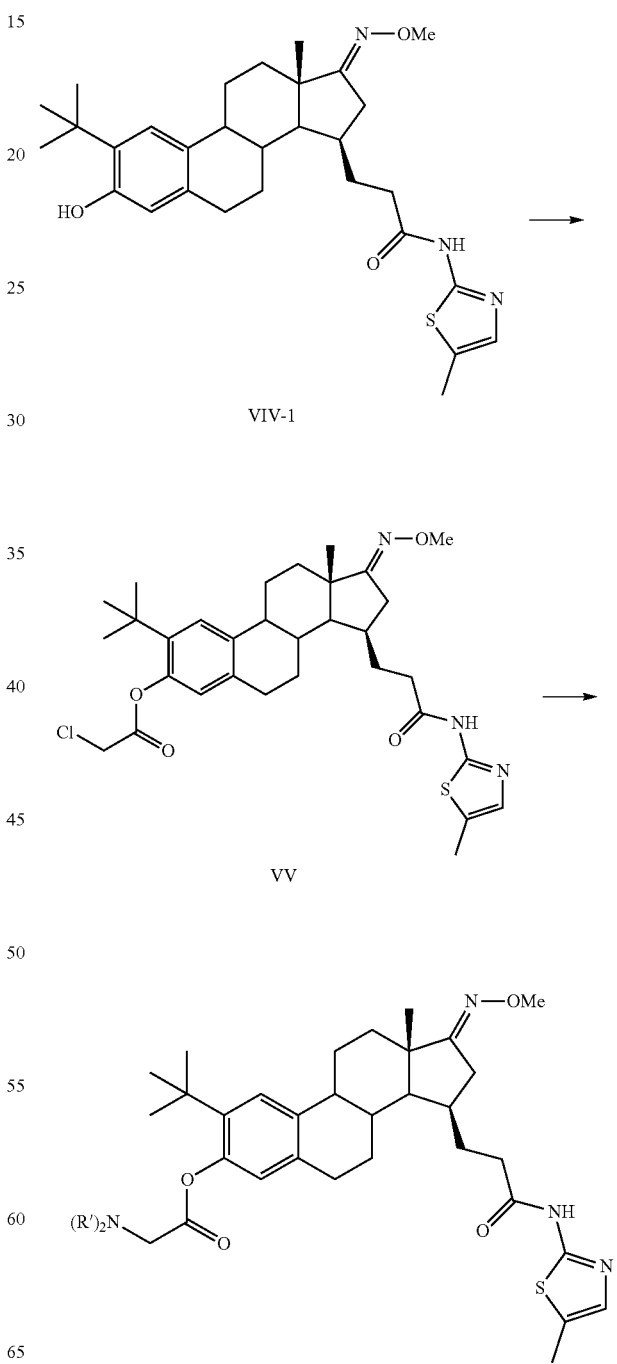

Compound VV-1

(13S,15R)-2-(tert-butyl)-17[(E)-methoxyimino]-13-methyl-15-(3-((5-methylthiazol-2-yl)amino)-3-oxo-propyl)-7,8,9,11,12,13,14,15,16,17-decahydro-6H-cyclopenta[a]phenanthren-3-yl 2-chloroacetate

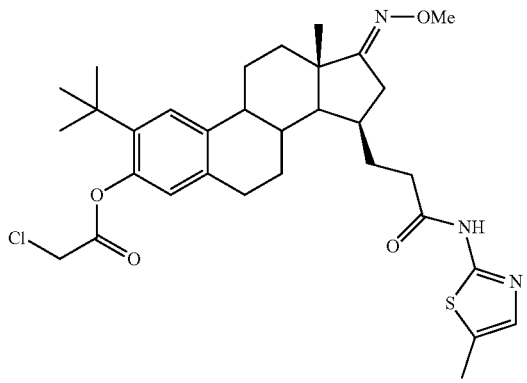 [SMILES: CO/N=C1\C[C@@H](CCC(=O)Nc2ncc(C)s2)C2C3CCc4cc(OC(=O)CCl)c(C(C)(C)C)cc4C3CC[C@]12C]

VIV-1 (500 mg, 0.95 mmol, 100 mol-%) was dissolved in dry DCM (5 ml) and pyridine (230 µl, 2.9 mmol, 300 mol-%) was added under nitrogen atmosphere. The reaction mixture was cooled with ice-bath and chloroacetyl chloride (230 µl, 2.9 mmol, 300 mol-%) dissolved in dry DCM (2 ml) was added dropwise. Stirring was continued in ice-bath for 2.5 hours. The reaction mixture was diluted with DCM (10 ml) and water (20 ml), the product was extracted in organic phase. Water phase was extracted with DCM (3×5 ml). Organic phases were combined and washed with 1N HCl (30 ml), 1N NaOH (3×20 ml), water (3×50 ml) and finally with brine (30 ml). The crude product 550 mg (96%) was used for further reactions without purification.

$^1$H NMR (200 MHz, DMSO-d$_6$) δ ppm 1.05 (s, 3H), 1.25 (s, 9H), 1.40-2.80 (m, 21H), 3.74 (s, 3H), 4.72 (s, 2H), 6.80 (s, 1H), 7.11 (s, 1H), 7.25 (s, 1H), 11.91 (br s, 1H).

Compound 7

(13S,15R)-2-(tert-butyl)-17[(E)-methoxyimino]-13-methyl-15-(3-((5-methylthiazol-2-yl)amino)-3-oxo-propyl)-7,8,9,11,12,13,14,15,16,17-decahydro-6H-cyclopenta[a]phenanthren-3-yl 2-morpholinoacetate

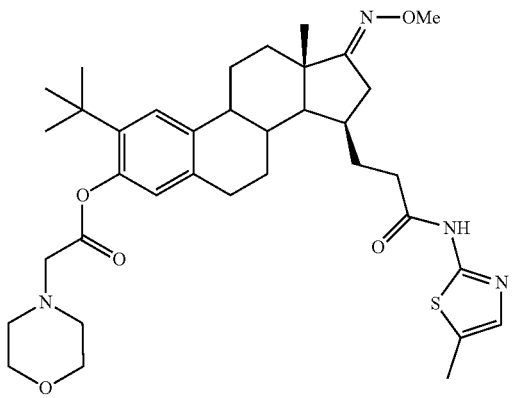 [SMILES: CO/N=C1\C[C@@H](CCC(=O)Nc2ncc(C)s2)C2C3CCc4cc(OC(=O)CN5CCOCC5)c(C(C)(C)C)cc4C3CC[C@]12C]

VV (200 mg, 0.33 mmol, 100 mol-%) was dissolved in dry THF (4 ml) and sodium iodide (150 mg, 1.0 mmol, 300 mo. %) was added, and stirred at rt for one hour under nitrogen. Then the reaction mixture was cooled with ice-bath and morpholine (43 µl, 0.50 mmol, 150 mol-%) was added dropwise as dissolved in THF (1 ml). Stirring was continued in cold for an hour, then at rt for two hours. The solvent was evaporated, and the precipitate was dissolved in EtOAc (10 ml) and the reaction mixture was poured to ice-cold 0.1N HCl-solution. The phases were separated. Water phase was extracted with EtOAc (3×5 ml). Organic phases were combined and washed with water (3×30 ml) and finally with brine (3×20 ml). After drying with MgSO4 the solvent was evaporated yielding the product 192 mg; the yield was 89%.

$^1$H NMR (200 MHz, DMSO-d$_6$) δ ppm 1.05 (s, 3H), 1.27 (s, 9H), 1.40-2.92 (m, 28H), 3.73 (s, 3H), 4.59 (s, 2H), 6.89 (s, 1H), 7.12 (s, 1H), 7.27 (s, 1H), 10.67 (br s, 1H), 11.96 (br s, 1H).

Compound 8

(13S,15R)-2-(tert-butyl)-17[(E)-methoxyimino]-13-methyl-15-(3-((5-methylthiazol-2-yl)amino)-3-oxo-propyl)-7,8,9,11,12,13,14,15,16,17-decahydro-6H-cyclopenta[a]phenanthren-3-yl triethylglycinate, chloride salt

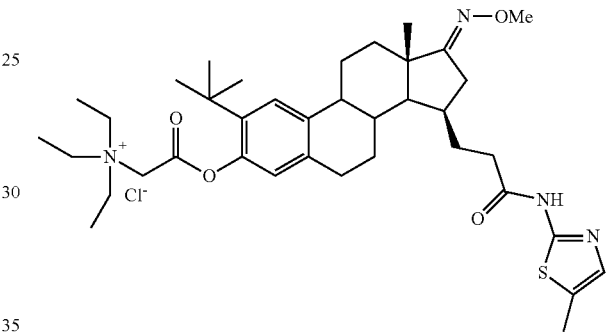

Triethylglycinate was prepared by the same method as described for the compound 7 using VV as a starting material and triethylamine (150 mol-%) as a reagent. The product was purified by chromatography.

$^1$H NMR (200 MHz, DMSO-d$_6$) δ ppm 1.05 (s, 3H), 1.27 (m, 18H), 1.48-2.81 (m, 21H), 3.57 (q, 6H), 3.73 (s, 3H), 4.80 (s, 2H), 6.89 (s, 1H), 7.11 (s, 1H), 7.28 (s, 1H), 11.91 (br s, 1H).

Compound 9

(13S,15R)-2-(tert-butyl)-17[(E)-methoxyimino]-13-methyl-15-(3-((5-methylthiazol-2-yl)amino)-3-oxo-propyl)-7,8,9,11,12,13,14,15,16,17-decahydro-6H-cyclopenta[a]phenanthren-3-yl isopropylglycinate

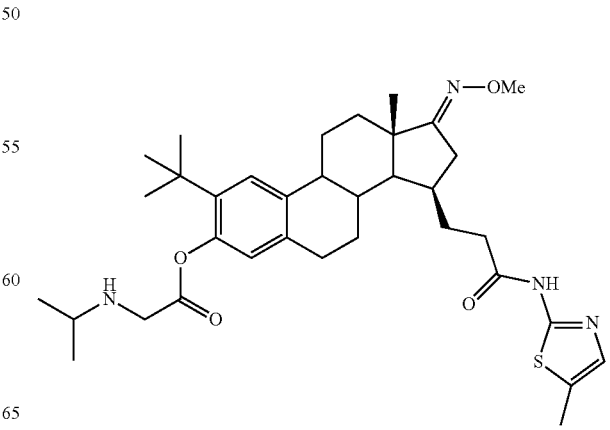

VV (100 mg, 0.17 mmol, 100 mol-%) was dissolved in dry THF (4 ml) and NaI (125 mg, 0.83 mmol, 500 mol-%) was added. Reaction was stirred at rt for 0.5 hours. Reaction was cooled to 0° C. with ice-bath and isopropylamine (165 μl, 2.01 mmol, 1200 mol-%) dissolved in dry THF (1 ml) was added dropwise. Reaction was stirred at 0° C. for 5 hours. EtOAc (5 ml) was added and reaction mixture was poured in ice-cold water (5 ml). Layers were separated and water layer was extracted with EtOAc (3×5 ml). Combined organic layers were extracted with water (3×5 ml) and brine (3×5 ml) and dried with MgSO$_4$. Crude product was purified by flash chromatography. Amount of the product was 35 mg.

$^1$H NMR (200 MHz, DMSO-d$_6$) δ ppm 0.98 (s, 3H), 1.01 (s, 3H), 1.05 (s, 3H), 1.26 (s, 9H), 1.12-2.90 (m, 23H), 3.62 (br s, 2H), 3.73 (s, 3H), 6.71 (s, 1H), 7.11 (s, 1H), 7.23 (s, 1H), 11.90 (br s, 1H)

Compound 9a (13S,15R)-2-(tert-butyl)-17[(E)-methoxyimino]-13-methyl-15-(3-((5-methylthiazol-2-yl)amino)-3-oxo-propyl)-7,8,9,11,12,13,14,15,16,17-decahydro-6H-cyclopenta[a]phenanthren-3-yl isopropylglycinate hydrochloride

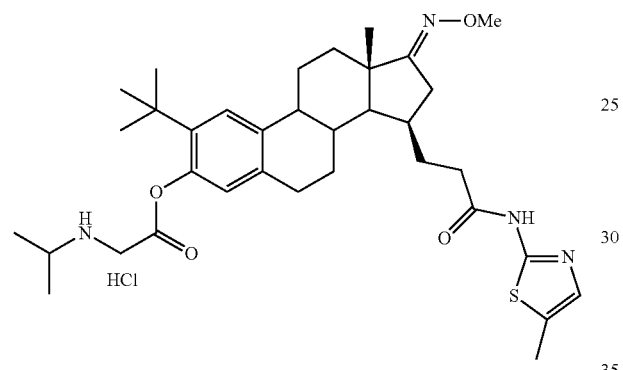

9 (300 mg, 0.52 mmol) was dissolved in dry EtOAc (1 ml). Conc. HCl (34 μl) dissolved in dry EtOAc (0.2 ml) was added (pH ~1) and reaction stirred at rt for 1 hour. Solvent was evaporated and co-evaporated with toluene. Crude product was triturated with EtOAc (3×1 ml) and Et$_2$O (5×1 ml). Amount of the product 41 mg.

$^1$H NMR (200 MHz, DMSO-d$_6$) δ ppm 1.05 (s, 3H), 1.29 (s, 9H), 1.31 (s, 6H), 1.49-2.90 (m, 17H), 3.41 (m, 1H), 3.73 (s, 3H), 4.34 (t, 2H), 6.80 (s, 1H), 7.11 (s, 1H), 7.28 (s, 1H), 9.35 (br s, 2H), 11.94 (s, 1H), 11.90 (br s, 1H).

Synthesis of Other C-3 Derivatives

Compound 10

Acetic acid (13S,15R)-2-tert-butyl-13-methyl-17[(E)-methoxyimino]-15-[2-(5-methyl-thiazol-2-yl-carbamoyl)-ethyl]-7,8,9,11,12,13,14,15,16,17-deca-hydro-6H-cyclopenta[a]phenanthren-3-yl ester

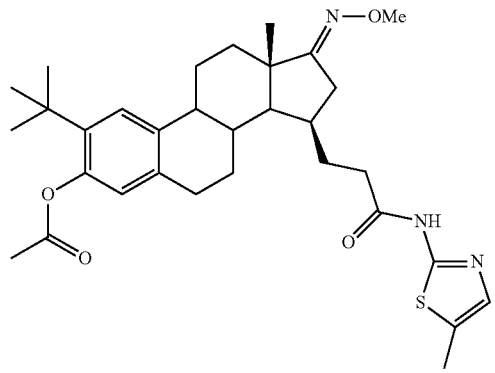 [SMILES: CO/N=C1\C[C@@H](CCC(=O)Nc2ncc(C)s2)C2C3CCc4cc(OC(C)=O)c(C(C)(C)C)cc4C3CC[C@]12C]

VIV-1 (500 mg, 0.95 mmol, 100 mol-%) was dissolved in dry DCM (10 ml). Pyridine (930 μl, ~11 mmol, ~1200 mol-%) and acetic anhydride (450 μl, 4.8 mmol, 500 mol-%) were added, and the reaction mixture was stirred at rt for 2 hours. After dilution with DCM (10 ml), the product was washed with 2N HCl-solution (3×20 ml), water (3×30 ml) and finally with brine (3×20 ml), and dried with sodium sulphate.

$^1$H NMR (200 MHz, DMSO-d$_6$) δ ppm 1.05 (s, 3H), 1.27 (s, 9H), 1.29-1.47 (m, 3H), 1.79-2.10 (m, 6H), 2.23-2.44 (m, 13H), 2.67-2.83 (m, 2H), 3.73 (s, 3H), 6.71 (s, 1H), 7.11 (d, 1H), 7.23 (s, 1H), 11.90 (br s, 1H). MS m/z (TOF ES+): 588 (M+Na)+

Compound 11a (13S,15R)-2-(tert-butyl)-17[(E)-methoxyimino]-13-methyl-15-(3-((5-methylthiazol-2-yl)amino)-3-oxo-propyl)-7,8,9,11,12,13,14,15,16,17-decahydro-6H-cyclopenta[a]phenanthren-3-yl hydrogen sulphate, triethylammonium salt

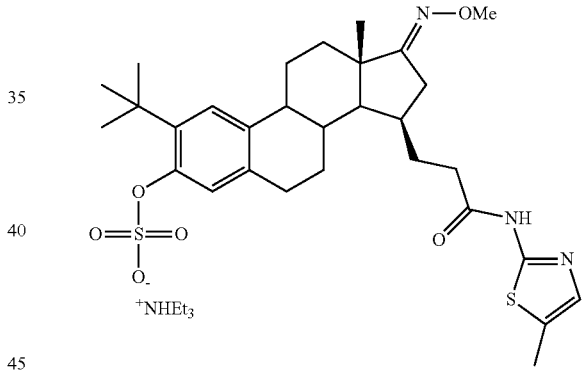

VIV-1 (0.4 g, 0.76 mmol, 100 mol-%) was dissolved in dry DMF (10 ml). Sulphur trioxide triethylamine complex (415 mg, 2.3 mmol, 300 mol-%) was added to the reaction mixture. Additional amount of the reagent (140 mg, 0.76 mmol, 100 mol-%) was added after two hours. The reaction mixture was stirred at rt over weekend. Silica gel (5 grams) was added and the solvent was evaporated (bath temperature below +35° C.). The product was eluted from silica by using toluene-ethanol-triethylamine (v/v 3:1:0.05), and the solvents were evaporated.

The precipitate was triturated several times with small portions of ethanol. The yield of triethylammonium salt was 288 mg; the yield was 53%.

$^1$H NMR (200 MHz, DMSO-d$_6$) δ ppm 1.05 (s, 3H), 1.17 (t, 9H), 1.30 (s, 9H), 1.40-2.81 (m, 22H), 3.09 (q, 6H), 3.73 (s, 3H), 7.08 (s, 1H), 7.11 (s, 1H), 7.31 (s, 1H), 11.91 (br s, 1H). MS m/z (TOF ES+): 705 M+

Compound 12

(13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl sulphamate

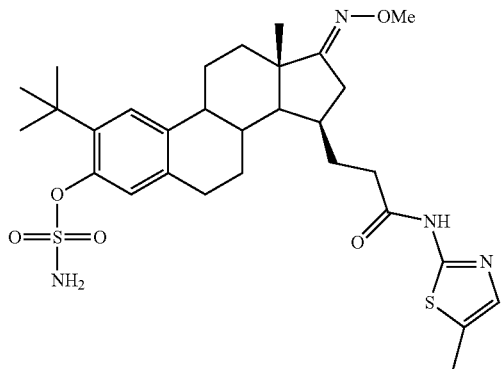 [SMILES: CO/N=C1\C[C@@H](CCC(=O)Nc2ncc(C)s2)C2C3CCc4cc(OS(N)(=O)=O)c(C(C)(C)C)cc4C3CC[C@]12C]

VIV-1 (100 mg, 0.191 mmol, 100 mol-%) and triethylamine (240 μl, 1.72 mmol, 900 mol-%) were dissolved in dry DCM (3 ml). Reaction was cooled to 0° C. with ice-bath. Sulfamoyl chloride (199 mg, 1.72 mmol, 900 mol-%) was dissolved in dry DCM (3 ml) and added in reaction. Reaction was stirred at rt for 2 days during which the sulfamoyl chloride reagent was added twice (2×90 mol-%). DCM (10 ml) was added and extracted with water (2×10 ml) and brine (10 ml). Crude product (110 mg) was purified by flash chromatography. Amount of the product was 25 mg. HPLC (218 nm) 9%.

$^1$H-NMR (DMSO-$d_6$): 1.04 (s, 3H), 1.33 (s, 9H), 1.20-2.90 (m, 21H), 3.72 (s, 3H), 7.11 (s, 1H), 7.23 (s, 2H), 8.13 (br s, 2H), 11.90 (br s, 1H).

Compound 13

(13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl 3-cyclopentylpropanoate

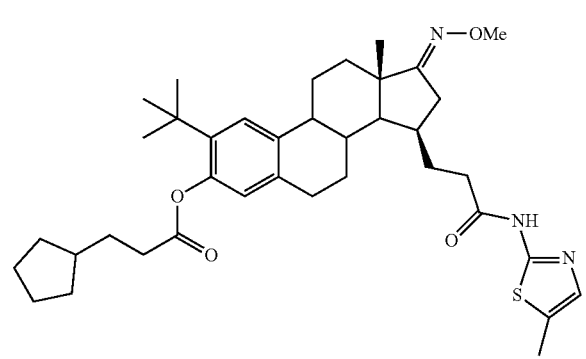 [SMILES: CO/N=C1\C[C@@H](CCC(=O)Nc2ncc(C)s2)C2C3CCc4cc(OC(=O)CCC5CCCC5)c(C(C)(C)C)cc4C3CC[C@]12C]

VIV-1 (0.4 g, 0.76 mmol) was dissolved in dry DCM (10 ml). Pyridine (620 μl, 7.6 mmol) and cyclopentanepropionyl chloride (590 μl, 3.8 mmol) were added under nitrogen atmosphere. The reaction mixture was refluxed until the reaction was completed (~6 hours). The reaction mixture was diluted with DCM (10 ml) and washed with water and several times with 1N HCl, followed by washing with water and brine. The crude product was purified by chromatography affording the product 254 mg; the yield was 51%.

$^1$H NMR (200 MHz, DMSO-$d_6$) δ ppm 1.04 (s, 3H), 1.25 (s, 9H), 1.44-2.70 (m, 32H), 2.67-2.83 (m, 2H), 3.72 (s, 3H), 6.68 (s, 1H), 7.10 (d, 1H), 7.22 (s, 1H), 11.89 (br s, 1H).

Compound 14

Di-tert-butyl((((13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)methyl) phosphate

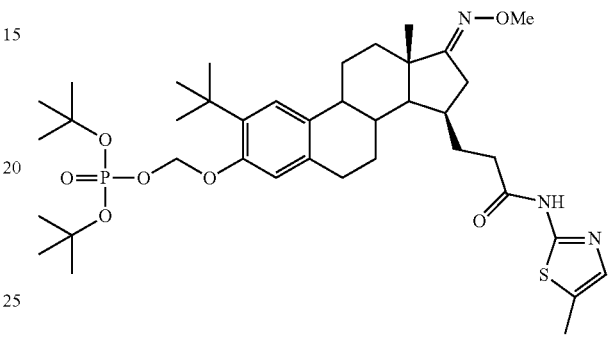

VIV-1 (400 mg, 0.764 mmol, 100 mol-%) was dissolved in dry DMF (10 ml). Di-tert-butyl chloromethyl phosphate [85%] (300 μl, 30 mol-%) and tetrabutylammoniumiodide (Bu$_4$NI) (56 mg, 20 mol-%) were added. Reaction was cooled to 0° C. NaH [60%] (68 mg, 1.68 mmol, 220 mol-%) was carefully added. Reaction was stirred first at 0° C. for 30 min and then at rt for 5 hours. Additional amounts of di-tert-butyl chloromethyl phosphate reagent in small proportions (33 mol-%) until the reaction was completed. Reaction was quenched with 10% citric acid (20 ml) and extracted with EtOAc (3×20 ml). Combined organic layers were extracted with 10% citric acid (1×20 ml), water (2×30 ml) and brine (2×30 ml) and dried with Na$_2$SO$_4$. The crude product was triturated with heptane:EtOAc (8:2) yielding 310 mg of the product.

$^1$H-NMR (DMSO-$d_6$): 1.04 (s, 3H), 1.10-2.90 (m, 21H), 1.32 (s, 9H), 1.41 (s, 18H), 3.73 (s, 3H), 5.57-5.63 (d, 2H), 6.83 (s, 1H), 7.11-7.13 (m, 2H), 11.91 (br s, 1H).

Compound 15

(((13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)methyl dihydrogen phosphate

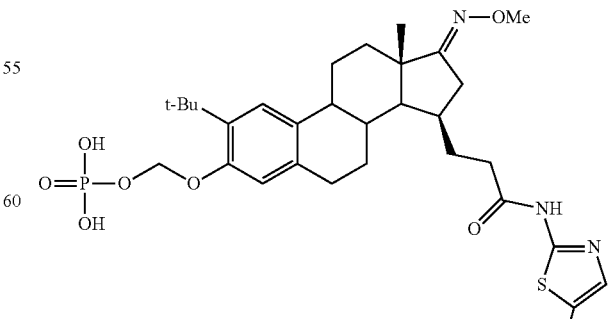

14 (300 mg) was dissolved in dry DCM (3 ml). Reaction was cooled to 0° C. Trifluoroacetic acid (62 µl) was dissolved in dry DCM (300 µl) and added in reaction. Reaction was stirred first at 0° C. for few hours and then at rt overnight. Additional amount of TFA (111 µl) was added and stirring continued. Total reaction time was three days. Solvent was evaporated. The crude product was purified by trituration with EtOAc and Et$_2$O yielding the product in 81 mg amount.

$^1$H-NMR (DMSO-d$_6$): 1.04 (s, 3H), 1.10-2.90 (m, 23H), 1.31 (s, 9H), 3.73 (s, 3H), 5.53-5.59 (d, 2H), 6.84 (s, 1H), 7.11 (m, 2H), 11.91 (br s, 1H).

Compound 15a (((13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)methyl dihydrogen phosphate disodium salt Disodium salt 15a was prepared by the same method as described for 1a.

$^1$H-NMR (D$_2$O): 0.90 (s, 3H), 0.90-2.80 (m, 21H), 1.30 (s, 9H), 3.75 (s, 3H), 5.44-5.47 (d, 2H), 6.99-7.15 (m, 3H).
$^{31}$P-NMR (D$_2$O): 1.38. MS m/z (TOF ES+): 634 [(M-2Na)+ H]+.

Compound 16 tert-Butyl ((13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl) carbonate

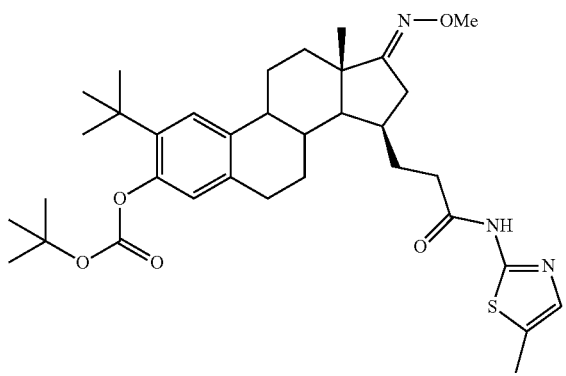 [SMILES: CO/N=C1\C[C@@H](CCC(=O)Nc2ncc(C)s2)C2C3CCc4cc(OC(=O)OC(C)(C)C)c(C(C)(C)C)cc4C3CC[C@]12C]

VIV-1 (100 mg, 0.191 mmol, 100 mol-%) was dissolved in dry DCM (2 ml). Triethylamine (133 µl, 0.955 mmol, 500 mol-%) was added. Reaction was cooled to 0° C. with ice-bath. Di-tert-butylpyrocarbonate (175 µl, 0.763 mmol, 400 mol-%) and DMAP (4 mg, 0.033 mmol, 17 mol-%) were added. Reaction was stirred 0° C. for 30 min, then at rt for ca. 25 hours. Di-tert-butylpyrocarbonate (175 µl) and DMAP (4 mg) were added and stirring continued for 3 hours. Reaction was poured in ice-water and extracted with DCM (3×10 ml). Combined organic layers were extracted with water (2×20 ml) and brine (2×20 ml). Crude product (165 mg) was purified by flash chromatography. Amount of the product was 114 mg.

$^1$H-NMR (DMSO-d$_6$): 1.04 (s, 3H), 1.26 (s, 9H), 1.46 (s, 9H), 1.10-2.90 (m, 21H), 3.73 (s, 3H), 6.73 (s, 1H), 7.10 (s, 1H), 7.21 (s, 1H), 11.90 (br s, 1H).

Compound 17

1-(tert-butyl)2-((13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl) pyrrolidine-1,2-dicarboxylate

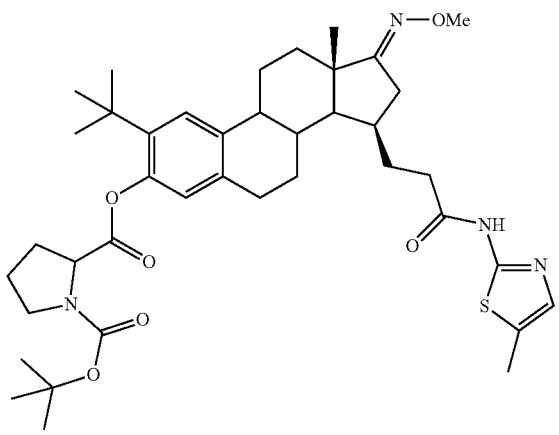 [SMILES: CO/N=C1\C[C@@H](CCC(=O)Nc2ncc(C)s2)C2C3CCc4cc(OC(=O)C5CCCN5C(=O)OC(C)(C)C)c(C(C)(C)C)cc4C3CC[C@]12C]

VIV-1 (500 mg, 0.955 mmol, 100 mol-%) was dissolved in dry DCM (10 ml) under nitrogen atmosphere. Pyridine (616 µl, 800 mol-%), BOC-Pro-OH (411 mg, 200 mol-%) and DCC (787 mg, 400 mol-%) were added to the reaction mixture. Reaction was stirred at rt for 4 h, at 40° C. for 2 h and overnight at rt. DMAP (30 mol-%) was added and stirring was continued at rt for 3 h. Oxalic acid (340 mg, 395 mol-%) dissolved in MeOH (1 ml) was added and stirring continued overnight at rt. The precipitated DHU was filtered off and solvents were evaporated. Residue was dissolved in DCM and washed with 0.5 N HCl (3×20 ml), water (3×20 ml) and brine (2×20 ml). The crude product was purified by chromatography and triturating with heptane. The amount of the product was 467 mg.

$^1$H-NMR (CDCl$_3$): 1.12 (s, 3H), 1.34 (s, 9H), 1.48 (s, 9H), 1.10-2.90 (m, 25H), 3.40-3.65 (m, 2H), 3.85 (s, 3H), 4.50-4.60 (m, 1H), 6.74-6.77 (m, 1H), 7.05 (s, 1H), 7.29 (s, 1H), 11.58 (br s, 1H).

Compound 18a (13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl prolinate 2,2,2-trifluoroacetate

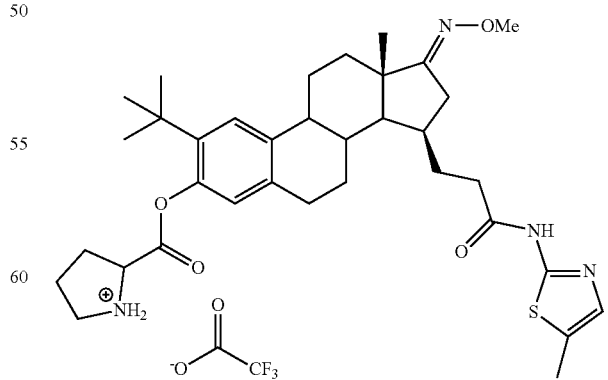

17 (450 mg, 0.624 mmol) was dissolved in dry DCM (5 ml) and cooled with ice bath. Trifluoroacetic acid (1.2 ml)

was added dropwise and the reaction mixture was stirred in ice bath for 4.5 hours. The solvent was evaporated and finally co-evaporated with toluene. The precipitate was triturated with Et$_2$O affording the TFA-salt 365 mg. Yield 80%.

$^1$H-NMR (CDCl$_3$): 1.10 (s, 3H), 1.30 (s, 9H), 1.10-2.90 (m, 25H), 3.40-3.60 (m, 2H), 3.85 (s, 3H), 4.60-4.80 (m, 1H), 6.68 (s, 1H), 7.05 (s, 1H), 7.29 (s, 1H).

Compound 18b (13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl prolinate hydrochloride

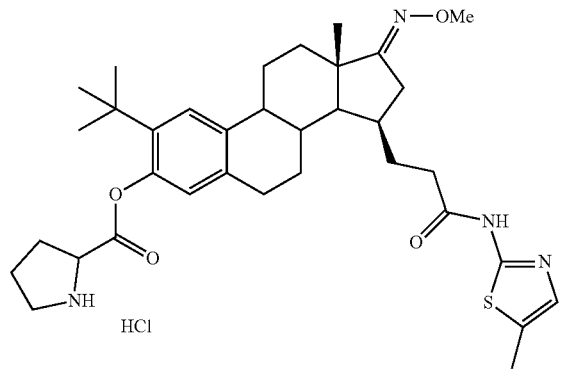 [SMILES: CO/N=C1\C[C@@H](CCC(=O)Nc2ncc(C)s2)C2C3CCc4cc(OC(=O)C5CCCN5)c(C(C)(C)C)cc4C3CC[C@]12C ; Cl]

TFA-salt 18a (60 mg, 0.082 mmol, 100 mol-%) was dissolved in EtOAc (1 ml) and 4M HCl-solution (45 µl) was added. The reaction mixture was stirred at rt for an hour, the solvent was evaporated, followed by co-evaporation with toluene. Residue was triturated with EtOAc. Precipitate was filtered and washed with EtOAc affording the HCl-salt (48 mg). Yield 88%.

$^1$H-NMR (DMSO-d$_6$): 1.05 (s, 3H), 1.27 (s, 9H), 1.10-2.90 (m, 25H), 3.15-3.40 (m, 2H), 3.73 (s, 3H), 4.60-4.80 (m, 1H), 6.90 (s, 1H), 7.11 (s, 1H), 7.27 (s, 1H), 9.27 (br s, 1H), 10.36 (br s, 1H), 11.95 (br s, 1H). MS m/z (TOF ES+): 621 (—HCl; M+1).

Pharmacological Tests

The following tests are provided to demonstrate the present invention in illustrative way and should not be considered as limiting in the scope of invention. Further, the concentrations of the compounds in the assays are exemplary and should not be taken as limiting. A person skilled in the art may define pharmaceutically relevant concentrations with method known in the art.

Inhibition of 17β-Hydroxysteroid Dehydrogenase Type 1 Enzyme

17β-HSD1 Production and Isolation:

Recombinant baculovirus was generated by the "Bac to Bac Expression System" (Invitrogen). Recombinant bacmid was transfected to Sd9 insect cells using "Cellfectin Reagent" (Invitrogen). 60 h later cells were harvested; the microsomal fraction was isolated as described by Puranen, T. J., Poutanen, M. H., Peltoketo, H. E., Vihko, P. T. and Vihko, R. K. (1994) Site-directed mutagenesis of the putative active site of human 17β-hydroxysteroid dehydrogenase type 1. Biochem. J. 304: 289-293. Aliquots were stored frozen until determination of enzymatic activity.

Assay—Inhibition of Recombinant Human 17β-HSD1:

Protein homogenate (0.1 µg/ml) was incubated in 20 mM KH2PO4 pH 7.4 with 30 nM estrone (including 800 000 cpm/ml of $^3$H-estrone) and 1 mM NADPH for 30 min at RT, in the presence of the potential inhibitor at concentrations 1 µM or 0.1 µM. Inhibitor stock solutions were prepared in DMSO. Final concentration of DMSO was adjusted to 1% in all samples. The enzyme reaction was stopped by addition of 10% trichloroacetic acid (final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of 1 ml/min in acetonitrile:water 48:52 as running solvent. Radioactivity was monitored in the eluate by a Packard Flow Scintillation Analyzer. Total radioactivity for estrone and estradiol were determined in each sample and percent conversion of estrone to estradiol was calculated according to the following formula:

$$\% \text{ conversion} = 100 \times \frac{\{(cpm\ estradiol\ \text{in sample with inihibitor})/[(cpm\ estrone\ \text{in sample with inhibitor}) + (cpm\ estradiol\ \text{in sample with inhibitor})]\}}{[(cpm\ estradiol\ \text{in sample without inihibitor})/[(cpm\ estrone\ \text{in sample without inhibitor}) + (cpm\ estradiol\ \text{in sample without inhibitor})]\}}$$

Percent inhibition was calculated flowingly: % inhibition=100−% conversion

The values % inhibition were determined for the parent compounds and the results are summarized in Table 3.

Inhibition of the 17β-Hydroxysteroid Dehydrogenase Type 2 Enzyme

17β-HSD2 Production and Isolation:

Similarly to 17β-HSD1 the Recombinant baculovirus was generated by the "Bac to Bac Expression System" (Invitrogen). Recombinant bacmid was transfected to Sd9 insect cells using "Cellfectin Reagent" (Invitrogen). 60 h later cells were harvested and supernatant were fractionated by the following protocol:

cells were dissolved into 40 ml of A-buffer (40 mM TRIS, pH8.0, 20% glycerol, 20 µM NAD, 0.4 mM PMSF, 150 mM NaCl, 0.5% dodecyl-β-maltoside+protease inhibitor cocktail)

cells were sonicated lysate was incubated on ice for 15 min lysate was centrifuged 5000 rpm 15 min, +4° C.

centrifugation of the supernatant 180 000 g 30 min, +4° C.

pellet was dissolved into 8 ml of A-buffer not resuspended material was removed by centrifugation 5000 rpm 15 min, +4° C.

the clear supernatant was divided into 100 µl aliquots and were stored frozen until determination of enzymatic activity.

The amount of 17β-HSD2 was analysed by immunoblotting and total protein concentration of each extract batch was determined.

Assay—Inhibition of Recombinant Human 17β-HSD2:

Protein homogenate (4 µg/ml) was incubated in 20 mM KH2PO4 pH 8.5 with 50 nM estradiol (including 800 000 cpm/ml of $^3$H-estradiol) and 1 mM NADH for 30 min at RT, in the presence of the potential inhibitor at concentrations 1 µM or 0.1 µM. Inhibitor stock solutions were prepared in DMSO. Final concentration of DMSO was adjusted to 1% in all samples. The enzyme reaction was stopped by addition of 10% trichloroacetic acid (final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of 1 ml/min in acetonitrile:water 48:52 as running solvent. Radioactivity was monitored in the eluate by a Packard Flow Scintillation Analyzer. Total radioactivity for estrone and estradiol were determined in each sample and percent conversion of estradiol to estrone was calculated according to the following formula:

$$\% \text{ conversion} = 100 \times \frac{\{(cpm\ estrone\ \text{in sample with inihibitor})/[(cpm\ estradiol\ \text{in sample with inhibitor}) + (cpm\ estrone\ \text{in sample with inhibitor})]\}}{[(cpm\ estrone\ \text{in sample without inihibitor})/[(cpm\ estradiol\ \text{in sample without inhibitor}) + (cpm\ estrone\ \text{in sample without inhibitor})]\}}$$

Percent inhibition was calculated flowingly: % inhibition=100−% conversion

The values % inhibition were determined for the active entities and the results are summarized in Table 3.

TABLE 3

Pharmacological activity of the active entities

| # | 17β-HDS1 Inhibition % at 1 μM | 17β-HSD2 Inhibition % at 1 μM |
|---|---|---|
| VIV-1 | 86 | 14 |
| VIV-3 | 95 | 41 |
| VIV-4 | 89 | 8 |

Estrogen Receptor Binding Assay

The binding affinity of the parent compounds to the estrogen receptor a (ERα) may be determined according to the in vitro ER binding assay described by Koffmann et al REF. Alternatively, an estrogen receptor binding assay may be performed according to international patent application WO2000/07996.

Estrogen Receptor Transactivation Assays

The parent compounds showing binding affinity towards the estrogen receptor may be further tested with regard to their individual estrogenic or antiestrogenic potential (Agonistic or antagonistic binding to the ERα or ERβ). The determination of the estrogen receptor antagonistic activity may be performed according to an in vitro assay system using the MMTV-ERE-LUC reporter system for example described in US patent application US2003/0170292.

Metabolic Stability Assay

The in vitro metabolic stability of the parent compounds was determined for exemplified compounds using human liver microsome and homogenate incubations. The incubation time points used with or without appropriate cofactors were 0 min and 60 min. Samples were collected at both time points and substrates were detected using LC/PDA/TOF-MS. In vitro metabolic stability (% remaining after 60 min in human liver homogenate or microsomes) of the compounds were calculated and the results are summarized in Table 4.

TABLE 4

Metabolic stability

| # | In vitro metabolic stability, % remaining after 60 min |
|---|---|
| VII | 13 |
| VIV-1 | 100 |
| VIV-3 | 100 |

Enzymatic Hydrolysis of Compounds of Formula (I)

Hydrolysis of the compounds according to Examples 1, 3a, 4a and 15a to their parent compound VIV-1 was tested. The unit amounts of alkaline phosphatase type VIIS from bovine intestinal mucosa were used as defined by a supplier (SigmaAldrich). An appropriate amount of compound (final concentration typically 50 μM) was dissolved in preheated buffer solution (pH 7.4) and the solutions were placed in a thermostatically controlled water bath at 37° C. The enzymatic reaction was started by adding enzyme to the solution. In blank solutions, enzyme was replaced with the same volume of water to ensure that the hydrolysis was clearly enzymatic. At predetermined time intervals, 200 μl samples were removed and 200 μl icecold acetonitrile was added to each sample to stop the enzymatic hydrolysis. The samples were kept on ice, centrifuged for 10 min at 14000 rpm, and the supernatant was analyzed by the HPLC. Pseudo-first order halflives (t1/2) for the hydrolysis of compounds were calculated from the slope of the linear portion of the plotted logarithm of the remaining compound versus time.

All tested compounds hydrolyzed to their corresponding parent molecules within about 3 to 8 min.

Aqueous Solubility Test

The aqueous solubility of the parent compounds VIV-1, VIV-2, VIV-3 and VIV-4 and the compounds of Examples 1, 1a, 3a, 4a and 15a was determined at rt in an appropriate buffer solution (0.16 M phosphate buffer or 0.05 mM TrisHCl buffer at pH 7.4, 0.05 M acetate buffer at pH 5.0, 50 mM (ionic strength 0.15) HCl buffer at pH 1.0). The pH of the mixtures was held constant during the study. Excess amounts or a known amount of each component are added to 1 or 0.5 ml of buffer solution and the mixtures were stirred at rt for 48 hours or less, filtered (0.45 um Millipore) and analyzed by HPLC. The results are presented in Table 5.

TABLE 5

Solubility data

| Compound | Aqueous solubility, buffer at pH 7.4 |
|---|---|
| VIV | under quantification limit (0.52 μg/ml) |
| 1a | over 32 mg/ml |
| 3a | 8.26 μg/ml |
| 4a | 7.99 μg/ml |
| 15a | over 30 mg/ml |

It will be seen from Table 5 that Examples 1, 1a, 3a, 4a and 15a exhibited improved aqueous solubility and that phosphoric acid derived compounds 1a and 15 show significant aqueous solubility.

Determination of Bioavailability

This study was performed in order to determine bioavailability of the present compounds in vivo. All animal experiments are performed in accordance with standards of ethical conduct and appropriate institutional animal care and use policies.

The pharmacokinetic studies of the parent compound VIV-1 and compounds of the invention were assessed in Cynomolgus monkeys. The study compounds were administrated orally at a dose level corresponding to 10 mg/kg of parent drug. The common aqueous formulation, 0.5% Carboxymethyl cellulose in water, was used as a vehicle. The blood samples were obtained by direct venipuncture at pre-dose, and ten sequential time points after oral administration.

The quantitative bioanalysis of plasma samples were performed in accordance with the guidance Bioanalytical Method Validation (FDA, 2001) and the Guideline on Bioanalytical Method Validation (European Medicines Agency, 2011). Analytical method was optimized for suitable chromatographic (peak shape, retention) and mass spectrometric (ionization efficiency) properties.

A non-compartmental pharmacokinetic analysis was carried out with individual plasma concentration-time curves using WinNonlin® Professional Version 6.3 (Pharsight Corporation): $C_{max}$ (maximum observed concentration) and $t_{max}$ (time taken to reach maximum observed concentration) values. The area under the concentration-time curve from 0 to the last measurable concentration ($AUC_t$) was calculated using the linear-log trapezoidal rule.

The obtained $C_{max}$ and $AUC_t$ values of study compounds are shown in Table 6.

TABLE 6

$C_{max}$ and $AUC_t$ values

| Compound | Cmax (ng/mL) | AUCt (ng · h/mL) |
|---|---|---|
| VIV | 61 | 692 |
| 1a | 274 | 2397 |
| 4a | 240 | 2348 |
| 6a | 147 | 1885 |
| 7 | 41 | 515 |
| 10 | 36 | 394 |
| 15a | 288 | 2893 |

It will be seen from Table 6 that all tested compounds of the invention provide at least comparable bioavailability as the active entity administered as such. However, the phosphoric acid derived compounds show significant improvement in bioavailability.

Utility of the Invention

Compounds of the invention when metabolized to their parent compounds and/or as such show selective inhibitory potential of the 17β-HSD1 enzyme and little or no inhibitory activity to the 17β-HSD2 enzyme and therefor, and may be useful for the treatment of a steroid hormone dependent malign or benign disease or disorder, in particular for treatment and prevention of several estrogen dependent diseases and disorders. Further, compounds of the present invention may be useful for the treatment of diseases and disorders associated with increased levels of estradiol and which may be prevented, treated, and/or ameliorated by an inhibitor of 17β-HSD1 enzyme.

Examples of inflammatory diseases and conditions include, but are not limited to, breast cancer, prostate carcinoma, ovarian cancer, uterine cancer, endometrial cancer, endometrial hyperplasia, endometriosis, uterine fibroids, uterine leiomyoma, adenomyosis, dysmenorrhea, menorrhagia, metrorrhagia, prostadynia, benign prostatic hyperplasia, urinary dysfunction, polycystic ovarian syndrome, lower urinary tract syndrome, multiple sclerosis, obesity, rheumatoid arthritis, colon cancer, tissue wounds, skin wrinkles and cataracts.

"Treatment or prevention" as used herein includes prophylaxis, or prevention of, as well as lowering the individual's risk of falling ill with the named disorder or condition, or alleviation, amelioration, elimination, or cure of the said disorder once it has been established.

Thus the compound of the present invention may be useful as active ingredients in pharmaceutical composition for treatment or prevention of a disease or disorder requiring the inhibition of 17β-HSD enzyme.

Compounds of the present invention may be administered in an effective amount within the dosage range of about 0.1 μg/kg to about 300 mg/kg, preferably between 1.0 μg/kg to 10 mg/kg body weight. Compounds of the present invention may be administered in a single daily dose, or the total daily dosage may be administered in divided doses of two, three or four times daily.

"An effective amount" refers to an amount of a compound that confers a therapeutic effect on the treated subject. The therapeutic effect may be objective (i.e. measurable by some test or marker) or subjective (i.e. subject gives an indication of or feels an effect). Such treatment need not necessarily completely ameliorate the condition of disease. Further, such treatment or prevention can be used in conjunction with other traditional treatments for reducing the condition known to those skilled in the art.

Compounds of the invention are most preferably used alone or in other active ingredients. Compounds of the invention may be administered by various routes, for example, parenteral, subcutaneous, intravenous, intraarticular, intrathecal, intramuscular, intraperitoneal, and by intradermal injections, and via transdermal, rectal, buccal, oromucosal, nasal, ocular routes and via inhalation and via implant. The pharmaceutical compositions including a compound of the present invention as active ingredient may further include pharmaceutically acceptable additives.

Compounds may be formulated into a suitable composition; suitable administration forms include, for example, solutions, dispersions, suspensions, powders, capsules, tablet, pills, controlled release capsules, controlled release tablets and controlled release pills. In addition to the pharmacologically active compounds, the pharmaceutical compositions of the compounds can contain suitable pharmaceutically acceptable carriers comprising excipients and auxiliaries that facilitate processing of the active compounds into preparations that can be used pharmaceutically.

Furthermore, compounds of formula (I) can be used as synthesis intermediates for the preparation of other compounds, in particular of other pharmaceutically active ingredients, which are obtainable from compounds of formula (I), for example by introduction of substituents or modification of functional groups.

It will be obvious to a person skilled in the art that, as the technology advances, the inventive concept can be implemented in various ways. The invention and its embodiments are not limited to the examples described above but may vary within the scope of the claims.

The invention claimed is:

1. A compound having formula (I)

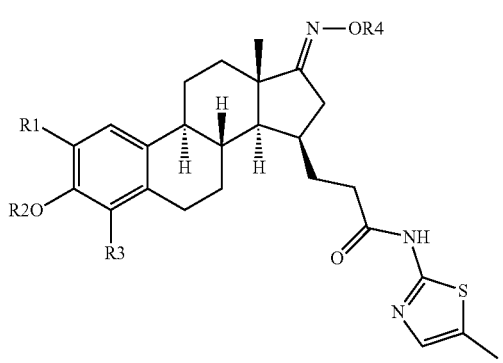

wherein
R1 is $C_{1-6}$-alkyl;
R2 is $(CH_2O)_m PO(OR')_2$;
R3 is H or halogen; and
R4 is H or $C_{1-3}$-alkyl;
whereby
R' is H, $C_{1-6}$-alkyl, $C_{1-3}$-haloalkyl, or $C_{1-3}$-perhaloalkyl; and
m is 0 or 1;
or a pharmaceutically acceptable salt thereof.

2. A compound of formula (I) as claimed in claim 1, or a pharmaceutically acceptable salt thereof, wherein R1 is t-Bu.

3. A compound of formula (I) as claimed in claim 1, or a pharmaceutically acceptable salt thereof, wherein R4 is methyl.

4. A compound of formula (I) as claimed in claim 1, or a pharmaceutically acceptable salt thereof, wherein R3 is H.

5. A compound of formula (I) as claimed in claim 1, or a pharmaceutically acceptable salt thereof, wherein m is 1.

6. A compound of formula (I) selected from the group consisting of:

Compound 1 Phosphoric acid mono-{(13S,15R)-2-tert-butyl-17[(E)-methoxyimino]-13-methyl-15-[2-(5-methylthiazol-2-ylcarbamoyl)ethyl-7,8,9,11,12,13,14,15,16,17-decahydro-6H-cyclopenta[a]phenanthren-3-yl} ester;

Compound 14 Di-tert-butyl((((13S,15R,E)-2-(tert-butyl)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)methyl) phosphate;

Compound 15 (((13S,15R)-2-(tert-butyl)-17[(E)-methoxyimino]-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy) methyl dihydrogen phosphate;

or a pharmaceutically acceptable salt thereof.

7. A pharmaceutical composition comprising an effective amount of one or more compounds as claimed in claim 1, together with one or more pharmaceutically acceptable excipient(s).

8. A pharmaceutical composition comprising an effective amount of one or more compounds or pharmaceutically acceptable salts as claimed in claim 1, together with one or more pharmaceutically acceptable excipient(s) in combination with one or more other active ingredients.

9. A method of alleviating or ameliorating a steroid hormone dependent malign or benign disease or disorder in a patient having said disease or disorder, the method comprising administering a compound or pharmaceutically acceptable salt as claimed in claim 1 to the patient.

10. The method of claim 9, wherein said disease or disorder is an estradiol dependent disease or disorder.

11. A method alleviating or ameliorating a steroid hormone dependent malign or benign disease or disorder in a patient having said disease or disorder, the disease or disorder being selected from the group consisting of breast cancer, prostate carcinoma, ovarian cancer, uterine cancer, endometrial cancer, endometrial hyperplasia, endometriosis, uterine fibroids, uterine leiomyoma, adenomyosis, dysmenorrhea, menorrhagia, metrorrhagia, prostadynia, benign prostatic hyperplasia, urinary dysfunction, polycystic ovarian syndrome, lower urinary tract syndrome, multiple sclerosis, obesity, rheumatoid arthritis, colon cancer, tissue wounds, skin wrinkles and cataracts, comprising administering a compound or pharmaceutically acceptable salt as claimed in claim 1 to the patient.

12. A method of alleviating or ameliorating a disease or disorder requiring the inhibition of 17β-HSD enzyme in a patient having said disease or disorder, the method comprising administering a compound or pharmaceutically acceptable salt as claimed in claim 1 to the patient.

* * * * *